(12) United States Patent
Crutchfield et al.

(10) Patent No.: US 12,311,183 B2
(45) Date of Patent: May 27, 2025

(54) CURRENT STEERING FOR CARDIAC PACING

(71) Applicant: Medtronic, Inc., Minneapolis, MN (US)

(72) Inventors: Randolph E. Crutchfield, Scottsdale, AZ (US); James J. St. Martin, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 518 days.

(21) Appl. No.: 17/465,673

(22) Filed: Sep. 2, 2021

(65) Prior Publication Data

US 2022/0088391 A1    Mar. 24, 2022

Related U.S. Application Data

(60) Provisional application No. 63/080,891, filed on Sep. 21, 2020.

(51) Int. Cl.
| | |
|---|---|
| *A61N 1/36* | (2006.01) |
| *A61N 1/02* | (2006.01) |
| *A61N 1/368* | (2006.01) |
| *A61N 1/05* | (2006.01) |
| *A61N 1/375* | (2006.01) |

(52) U.S. Cl.
CPC ........... *A61N 1/3686* (2013.01); *A61N 1/025* (2013.01); *A61N 1/0587* (2013.01); *A61N 1/37516* (2017.08)

(58) Field of Classification Search
CPC .... A61N 1/3686; A61N 1/025; A61N 1/0587; A61N 1/37516
See application file for complete search history.

(56) References Cited

U.S. PATENT DOCUMENTS

| | | |
|---|---|---|
| 5,117,824 A | 6/1992 | Keimel et al. |
| 5,545,186 A | 8/1996 | Olson et al. |

(Continued)

OTHER PUBLICATIONS

Sheikholeslami, "Source Degeneration," Circuit Intuitions, IEEE Solid-State Circuits Magazine, 10.1109/MSSC.2014.2329233, Aug. 26, 2014, pp. 5-6.

(Continued)

*Primary Examiner* — Rex R Holmes
(74) *Attorney, Agent, or Firm* — Shumaker & Sieffert, P.A.

(57) ABSTRACT

The disclosure describes capturing the cardiac tissue using current steering techniques with a multi-pole cardiac lead implanted near the cardiac tissue. The techniques may include current-controlled sources in an IMD to provide current regulation to the pacing pulses allowing direct stimulation through multiple electrode contacts with known current delivery to the tissue. This current steering technique may use a delivery current source coupled to a delivery electrode and a receiving current source coupled to a receiving electrode to steer the current to the desired tissue to be stimulated. In some examples, different electrode pairs may be paced sequentially or together. In other examples, two or more electrodes may be considered the "delivery electrodes" and two or more electrodes may be considered the "receiving electrodes." In some examples a current-controlled source in the IMD may be implemented using a source degeneration circuit.

17 Claims, 8 Drawing Sheets

(56) References Cited

U.S. PATENT DOCUMENTS

| | | | |
|---|---|---|---|
| 5,755,736 | A | 5/1998 | Gillberg et al. |
| 6,622,048 | B1 * | 9/2003 | Mann ................ A61N 1/36071 607/46 |
| 6,909,917 | B2 | 6/2005 | Woods et al. |
| 7,805,189 | B2 | 9/2010 | Stein et al. |
| 8,265,769 | B2 | 9/2012 | Denison |
| 8,326,418 | B2 | 12/2012 | Sommer et al. |
| 8,538,523 | B2 | 9/2013 | Sommer et al. |
| 9,020,589 | B2 | 4/2015 | Torgerson |
| 9,056,206 | B2 | 6/2015 | Torgerson et al. |
| 9,259,571 | B2 | 2/2016 | Straka et al. |
| 9,320,901 | B2 | 4/2016 | Torgerson et al. |
| 9,987,493 | B2 | 6/2018 | Torgerson et al. |
| 10,646,720 | B2 | 5/2020 | Reddy |
| 2007/0100399 | A1 | 5/2007 | Parramon et al. |
| 2012/0029600 | A1 | 2/2012 | Zhou et al. |
| 2013/0006332 | A1 | 1/2013 | Sommer et al. |
| 2016/0339248 | A1 * | 11/2016 | Schrock ............ A61N 1/36842 |
| 2018/0133494 | A1 | 5/2018 | Reddy |
| 2018/0345007 | A1 | 12/2018 | Parramon et al. |
| 2019/0143117 | A1 | 5/2019 | Ghosh |
| 2019/0280652 | A1 | 9/2019 | Schober et al. |

OTHER PUBLICATIONS

International Search Report and Written Opinion of International Application No. PCT/US2021/049854, dated Jan. 17, 2022, 9 pp.

* cited by examiner

CURRENT STEERING FOR CARDIAC PACING

This application claims the benefit of U.S. Provisional Patent Application 63/080,891, filed 21 Sep. 2020, the entire content of which is incorporated herein by reference.

TECHNICAL FIELD

The disclosure relates to circuitry for delivery of cardiac therapy by implantable medical devices.

BACKGROUND

For left ventricular pacing, a lead may be inserted next to the left ventricle, and an implantable medical device (IMD) may output voltage pacing pulse to capture, e.g. depolarize, the left ventricle. In some examples, an IMD may use a quad-pole lead, e.g. with four electrodes and select one or more of the four electrodes to capture the left ventricle. Selecting which of the electrodes to provide the voltage-controlled pacing pulse may depend on which combination of electrodes provides the best outcome for the patient.

SUMMARY

In general, the disclosure describes capturing, cardiac tissue, such as the left ventricle (LV) using current steering techniques, and not voltage-controlled pacing, with a multi-pole lead implanted adjacent to the left ventricle, e.g., in a cardiac vein. The techniques of this disclosure include current-controlled sources in an IMD to provide current regulation to the electrical current stimulation pulses (e.g., pacing pulses) allowing direct stimulation through multiple electrodes with known current delivery to the tissue, where known current delivery includes stimulation such that a clinician may configure the IMD to direct a desired current amplitude through a desired current path through tissue. Direct stimulation through multiple electrode contacts with known current amplitude may be beneficial because the clinician may achieve a desired medical outcome for the patient with improved control of stimulation therapy and reduced power consumption compared to other techniques.

Direct stimulation through multiple electrode contacts with known current amplitude, which may also be called current steering, may use a delivery current source coupled to a delivery electrode and a receiving current source coupled to a receiving electrode to steer the current to the desired tissue to be stimulated. In some examples, different electrode pairs may be paced sequentially or together. In other examples, two or more electrodes may be considered the "delivery electrodes" and two or more electrodes may be considered the "receiving electrodes."

In one example, the disclosure describes a medical system comprising: an implantable medical device coupled to a cardiac lead and configured to deliver pacing therapy to cardiac tissue of a heart via a plurality of electrodes of the cardiac lead. The implantable medical device comprises a first current source configured to output an electrical current stimulation pulse and a second current source configured to sink the electrical current stimulation pulse to capture a portion of the cardiac tissue as well as processing circuitry configured to: electrically connect the first current source to a first electrode of the plurality of electrodes to output the electrical current stimulation pulse to the cardiac tissue; and electrically connect the second current source to a second electrode of the plurality of electrodes to sink the electrical current stimulation pulse to the cardiac tissue.

In another example, the disclosure describes a method comprising: electrically connecting a first current source to a first electrode of a cardiac lead comprising a plurality of electrodes configured to be implanted proximate to cardiac tissue to output an electrical current simulation pulse; electrically connecting a second current source to a second electrode of the plurality of electrodes to sink the electrical current simulation pulse; and delivering the electrical current stimulation pulse to tissue of the cardiac tissue via the first electrode and the second electrode to capture a portion of the cardiac tissue.

In another example, the disclosure is directed to a computer-readable medium containing instructions. The instructions may cause processing circuitry, e.g. a programmable processor to electrically connect a first current source to a first electrode of a plurality of electrodes to output an electrical current stimulation pulse to cardiac tissue; and electrically connect a second current source to a second electrode of the plurality of electrodes to sink the electrical current stimulation pulse. A cardiac lead comprising the plurality of electrodes is coupled to the implantable medical device and the implantable medical device is configured to deliver pacing therapy to the cardiac tissue of a heart via the plurality of electrodes of the cardiac lead. The implantable medical device comprises the first current source configured to output an electrical current stimulation pulse and the second current source configured to sink the electrical current stimulation pulse to capture a portion of the cardiac tissue.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
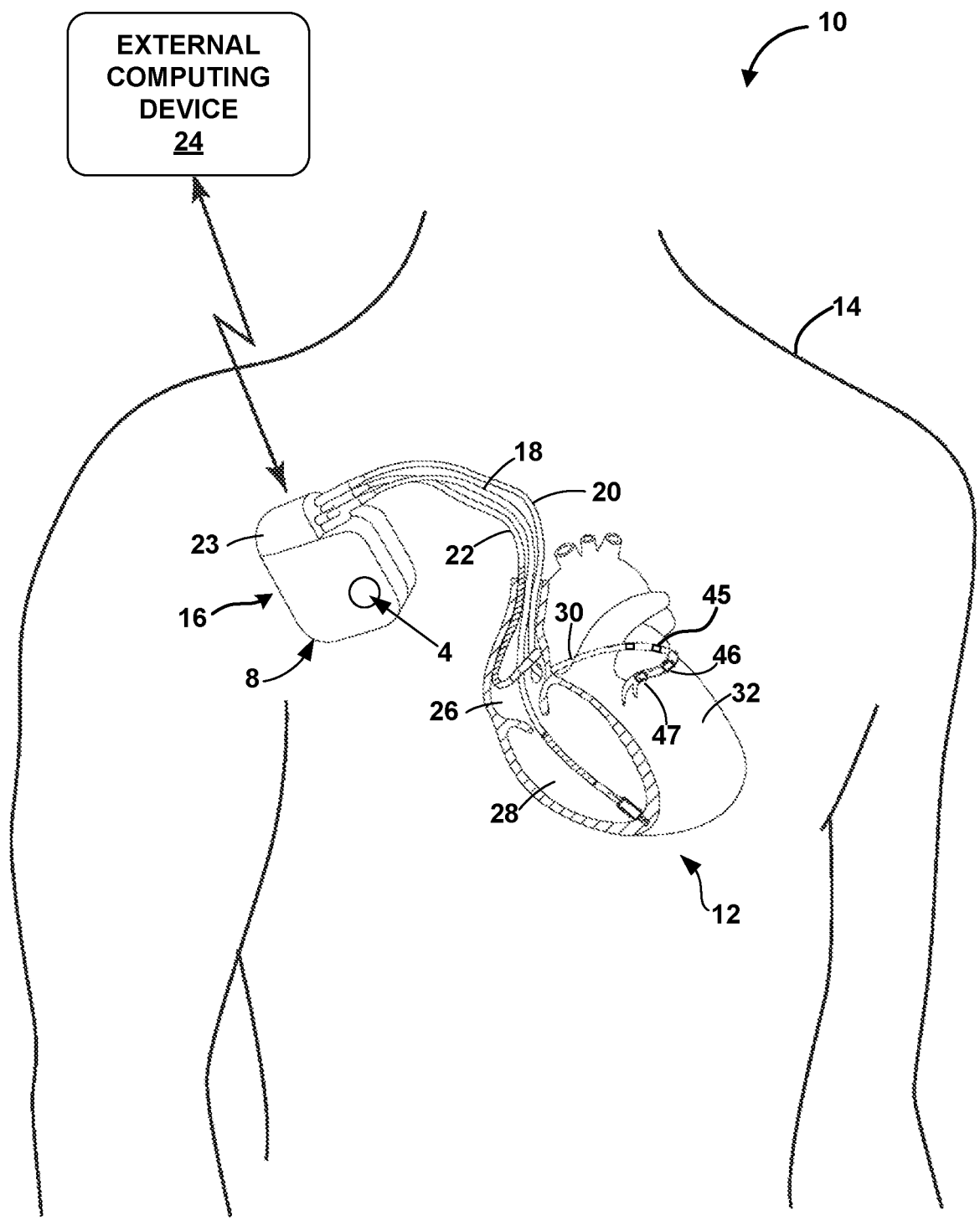
FIG. 1 is a conceptual diagram illustrating an example system for monitoring and treating cardiac events, which may include left ventricle (LV) pacing using current steering according to the techniques of this disclosure.

The disclosure describes capturing cardiac tissue, for example, the left ventricle (LV), using current steering techniques with a multi-pole lead implanted near the heart, such as in a cardiac vein. Capturing cardiac tissue may refer to applying an electrical current stimulation pulse, or other pacing pulse to the cardiac tissue causing depolarization and contraction.

The techniques of this disclosure include current-controlled sources in an implantable medical device to provide current regulation to the electrical current stimulation pulses (i.e., pacing pulses) allowing direct stimulation through multiple electrodes with known current delivery to the tissue. In accordance with one or more examples described in this disclosure, the electrical stimulation pulses may be current stimulation pulses, and therefore, the pacing pulses may be referred to as electrical current stimulation pulses. For instance, the implantable medical device may include multiple current sources to output (e.g., source) and sink the electrical current stimulation pulses through electrodes, and processing circuitry may select which electrodes to output and sink the electrical current stimulation pulses.

Current steering refers to techniques to selectively couple electrodes to different current sources to steer the path of the electrical current, and hence the electrical field generated by the electrical current. Current steering techniques may use a delivery current source coupled to a delivery electrode and a receiving current source coupled to a receiving electrode to steer the current to the desired tissue to be stimulated. In some examples, different electrode pairs may be paced sequentially or together. In other examples, two or more electrodes may be considered the "delivery electrode" and two or more electrodes may be considered the "receiving electrode."

The current steering techniques from within a cardiac vein of this disclosure may provide advantages over other pacing techniques. When compared to voltage-controlled pacing, which use a voltage-controlled source, the impedance of the electrode-tissue interface at each active contact will dictate current flow in the tissue. In turn, while these voltage-controlled pacing may allow for simultaneous activation of multiple contacts at a single voltage level, the clinician may not be able to directly control current flow across the contacts. Moreover, using an intracardiac multi-pole (i.e., a multi-electrode) lead, for example within a cardiac vein, may provide precise selection of the cardiac tissue to be stimulated when compared to a current steering lead placed in other locations. In particular, field steering directs the energy to an optimal tissue location while avoiding undesirable areas (e.g. phrenic nerve).

The techniques of this disclosure may allow capture of the cardiac tissue using reduced energy pacing pulses when compared to other techniques. In some examples, by precisely targeting the cardiac tissue to be stimulated, an IMD of this disclosure may use a lower energy electrical current stimulation pulse, e.g. a reduced amplitude and/or pulse width, and cause depolarization and contraction of the targeted cardiac tissue. Reduced energy pulses may provide better outcomes for a patient, including increased battery longevity and therefore longer times between battery replacement or recharging. Battery replacement may require surgery to replace a device, therefore, reducing the number of replaced devices may reduce patient cost, inconvenience, and risk of infection.

FIG. 1 is a conceptual diagram illustrating an example system 10 for monitoring and treating cardiac events, which may include LV pacing using current steering according to the techniques of this disclosure. Example system 10 in FIG. 1, may include an IMD 16, such as an implantable cardiac pacemaker, implantable cardioverter/defibrillator (ICD), or pacemaker/cardioverter/defibrillator. IMD 16 connects to leads 18, 20 and 22 and is communicatively coupled to external computing device 24. IMD 16 senses electrical signals attendant to the depolarization and repolarization of heart 12, e.g., a cardiac electrogram (EGM), via electrodes on one or more leads 18, 20 and 22 or the housing of IMD 16. IMD 16 may also deliver therapy in the form of electrical signals to heart 12 via electrodes located on one or more leads 18, 20 and 22 or a housing of IMD 16. The delivered therapy may be pacing, cardioversion and/or defibrillation pulses. IMD 16 may monitor EGM signals collected by electrodes on leads 18, 20 or 22, and based on the EGM signal, diagnose, and treat cardiac episodes.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

Lead 20 may be a multi-electrode, or multi-polar lead. In the example in which lead 20 includes four electrodes, lead 20 may be referred to as a quadripolar LV lead. To simplify FIG. 1, only three electrodes are labeled, electrodes 45, 46 and 47. In other examples, lead 20 may include more or fewer electrodes. In some examples, LV lead 20 comprises segmented electrodes, e.g., in which each of a plurality of longitudinal electrode positions of the lead, includes a plurality of discrete electrodes arranged at respective circumferential positions around the circumference of lead.

In some examples, IMD 16 includes one or more housing electrodes, such as housing electrode 4. Housing electrode 4 may be formed integrally with an outer surface of hermetically-sealed housing 8 of IMD 16 or otherwise coupled to housing 8. In some examples, housing electrode 4 is defined by an uninsulated portion of an outward facing portion of housing 8 of IMD 16. Other divisions between insulated and uninsulated portions of housing 8 may be employed to define two or more housing electrodes. In some examples, a housing electrode comprises substantially all of housing 8. In other examples, an electrode may be included in header 23 of IMD 16 and be referred to as an indifferent electrode.

Housing 8 encloses a signal generator that generates therapeutic stimulation, such as cardiac pacing, cardioversion, and defibrillation pulses, as well as a sensing module for sensing electrical signals attendant to the depolarization and repolarization of heart 12. Housing 8 may also enclose one or more processors coupled to a memory for storing the sensed electrical signals. Housing 8 may also enclose a telemetry module for communication between IMD 16 and external computing device 24.

IMD 16 may be configured to sense electrical signals attendant to the depolarization and repolarization of heart 12 via electrodes of leads 18, 20, 22 and housing electrode 4. IMD 16 may sense such electrical signals via any bipolar combination of electrodes of leads 18, 20, 22. Furthermore, any of the electrodes may be used for unipolar sensing in combination with housing electrode 4.

The illustrated numbers and configurations of leads 18, 20 and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intracardiac leads 18, 20 and 22, system 10 may include one or more leads not positioned within heart 12. Some examples of other leads may include an epicardial lead, a subcutaneous lead, a substernal lead, and esophageal lead, and so on. In some examples, a combination of electrodes on an intracardiac lead, along with electrodes in other locations, may provide precise steering of stimulation energy to specific tissue.

In some examples, external computing device 24 takes the form of a handheld computing device, computer workstation or networked computing device that includes a user interface for presenting information to and receiving input from a user. A user, such as a physician, technician, surgeon, electro-physiologist, or other clinician, may interact with external computing device 24 to retrieve physiological or diagnostic information from IMD 16. A user may also interact with external computing device 24 to program IMD 16, e.g., select values for operational parameters of the IMD. External computing device 24 may include a processing circuitry configured to evaluate EGM signals transmitted from IMD 16 to external computing device 24.

IMD 16 and external computing device 24 may communicate via wireless communication using any of techniques. Examples of communication techniques may include, for example, low frequency or radiofrequency (RF) telemetry. Other techniques, such as BLUETOOTH, Medical Implant Communication System (MICS), and similar techniques. In some examples, external computing device 24 may include a programming head that may be placed proximate to the patient's body near the implant site for IMD 16 to improve the quality or security of communication between IMD 16 and external computing device 24. In some examples, external computing device 24 may be located remotely from IMD 16 and communicate with IMD 16 via a network. External computing device 24 may also communicate with one or more other external devices using any one or more communication techniques, both wired and wireless, such as Ethernet, Wi-Fi, and similar techniques.

LV lead 20 is an example of an implantable LV lead comprising a plurality of electrodes, wherein the plurality of electrodes includes at least one bipolar electrode pair configured to sense a LV bipolar cardiac electrogram signal of tissue of the left ventricle 32 of heart 12 proximate the bipolar electrode pair. In some examples, IMD 16 comprises a signal generator configured to deliver cardiac pacing pulses to left ventricle 32 of heart 12 via at least one of the plurality of electrodes of LV lead 20.

Pacing in the left ventricle may be helpful for patients with certain conditions, such as a bundle branch block causing an uncoordinated contraction of the heart or congestive heart failure (CHF) patients. In some examples, IMD 16 may deliver voltage-controlled pacing pulses to capture, e.g. depolarize, the left ventricle. The techniques of this disclosure include IMD 16 with circuitry and LV lead 20 configured to deliver current controlled pacing, e.g. electrical current stimulation pulses, to stimulate and capture the left ventricle. By using electrical current stimulation pulse and current steering techniques, an IMD of this disclosure may more precisely steer the electrical current stimulation pulses to the targeted cardiac tissue to ensure the heart contracts in a coordinated manner to efficiently pump blood for the patient.

In this disclosure, a selected pacing vector, e.g. between two or more electrodes of LV lead 20, may cause a current path through the cardiac tissue between the selected electrodes. When the amplitude, or other characteristics of the pacing pulse, e.g. the electrical current stimulation pulse, satisfy the pacing threshold for the cardiac tissue in contact with the electrodes, the pacing pulse may cause depolarization of the cardiac tissue in and around the current path. In other words, the selected pacing vector may capture the selected portion of the cardiac tissue, which may conduct through the cardiac tissue to the rest of the left ventricle and cause a contraction. During implant, a clinician may select different pacing vectors and observe the results to determine which electrode selections, and which resulting current paths, provide the best outcome for the patient.

Pacing between two LV electrodes, e.g., between electrode 46 and 47 may be called bipolar pacing. Pacing between any one of the LV electrodes and housing electrode 4 may be called unipolar pacing. A bipolar stimulation arrangement, i.e., an arrangement in which an electrode, such as electrode 45 acts as an anode delivering current, and a second electrode e.g., 46 acts as a cathode receiving current, may provide stimulation fields that are small and have localized shapes. The small stimulation field is caused by the close proximity between the anodes and cathodes as compared to the sphere-like field created by a unipolar stimulation arrangement. A bipolar stimulation arrangement may produce a localized and tightly constrained stimulation. In this manner, a bipolar stimulation arrangement producing such a localized and tightly constrained stimulation field may be useful in specifically targeting one or more stimulation sites of a patient.

An example unipolar stimulation arrangement may be one in which housing electrode 4, or some other electrode in the header or on the housing is configured as an anode and sources current. An electrode on another lead, such as RV coil, RV ring, RA tip, on RV lead 18 or one of electrodes 45, 46 or 47 on LV lead 20 is configured as a cathode and sinks current. A unipolar configuration may be desirable for lower power consumption that results from the low impedance path through the tissue of patient 14, the stimulation field produced by a unipolar stimulation arrangement may resemble a large sphere, in contrast to the localized field for a bipolar arrangement.

In other examples, multiple anodes and/or multiple cathodes on one or more leads may be used to create a stimulation field in multipolar stimulation arrangement. Combining aspects of a bipolar stimulation arrangement, with aspects of a unipolar stimulation arrangement may deliver to a user more localized stimulation while consuming less power than would be achievable using bipolar stimulation. For example, housing electrode 4 may be configured as an anode, electrode 45 also configured as an anode and electrode 46 configured as a cathode, receiving current. In some examples, housing electrode 4 and electrode 45 may be configured to deliver equal amounts of current, e.g., 50% of the total current, while electrode 46 is configured to sink 100% of the current. In other examples, the delivered current from each electrode may be unequal, e.g., 60%-40%, 70%-30% or any other combination. Note that processing circuitry of IMD 16 may configure any combination of electrodes as sources or sinks and any percentage of current sourced or sunk from each electrode. The above examples are just for illustration.

In this manner a user effectively shapes, focuses or steers a stimulation field. Steering a stimulation field may allow a user to transition between a unipolar stimulation arrangement and a bipolar (or multipolar) stimulation arrangement or between a bipolar (or multipolar) arrangement and a unipolar arrangement, permitting the user to select different weighted combinations of current delivered to one or more lead cathodes by the housing anode and lead anode. The user may stop the transition at a desired point to use both a housing anode and at least one lead anode. In some examples, a user may configure one or more electrodes as anode "shields" on the lead that are in proximity to the cathodes. For example, electrodes 47 and 45 may be configured as cathodes and electrode 46, between electrodes 47 and 45, may be configured as an anode shield.

Figure 2A:
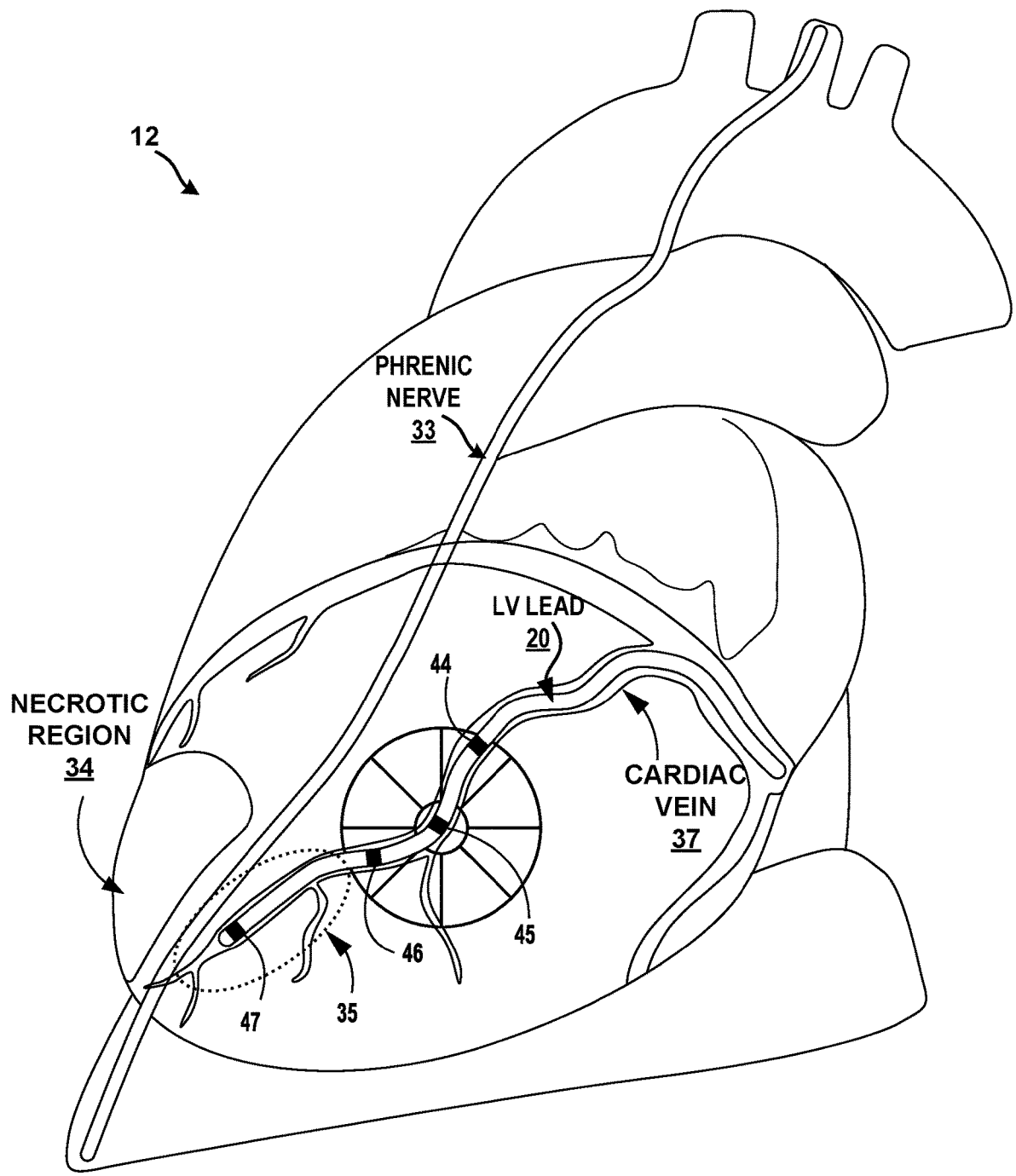
FIG. 2A is a is a conceptual diagram illustrating an example LV multi-polar lead implanted in a heart.

FIG. 2A is a conceptual diagram illustrating an example multi-polar lead implanted in a heart. In the example of FIG. 2A, heart 12 and LV lead 20 correspond to heart 12 and LV lead 20 and connected to IMD 16 described above in relation to FIG. 1. As described above in relation to FIG. 1, LV lead 20 may include a plurality of electrodes, e.g. electrodes 44-47, and may be placed in a cardiac vein near or on the left ventricle. Though shown with four electrodes in the example of FIG. 2A, LV lead 20 may include any number of electrodes. Although FIG. 2A describes a multi-polar lead implanted in a cardiac vein, in other examples, a multi-polar lead of this disclosure may be implanted in other regions proximal to heart 12, such as the right ventricle, right atrium or other locations.

Any one or more of electrodes 44-47 may be configured as the output or high side electrodes, or as the sink or low side electrodes. In some examples, depending on the desired current path, one or more electrodes in RV lead 18, RA lead 22, housing electrode 4, and indifferent electrode, or an electrode on a lead extension (not shown in FIG. 2A) may be configured as either the output or sink electrodes, in conjunction with any one or more LV lead electrodes, to steer current to the desired tissue to be stimulated. The output current may follow a current path between the output electrode(s) to the sink electrodes(s). The precise current path may depend on the conduction characteristics of the tissue between the output and sink electrodes. The clinician may select a pacing vector, e.g. between LV electrode 45 and LV electrode 46, between LV electrode 45 and housing electrode 4, or any other combination, such the current path that travels between the output and sink electrodes depolarizes the desired cardiac tissue.

The depolarization of the LV when paced may be different than intrinsic depolarization of the LV. For example, paced depolarization of the LV may generally progress from epicardial to endocardial tissue, and from the pacing site, while intrinsic depolarization may generally progress from endocardial to epicardial tissue, and from the Purkinje fibers.

In this disclosure, electrical capture occurs when a pacing stimulus, e.g. an electrical current stimulation pulse, leads to depolarization of the cardiac tissue and causes a contraction. A capture threshold is the minimum energy required to produce a depolarization of the paced chamber. The amount of energy in an electrical stimulation pulse may be controlled by, for example, a voltage magnitude, a current magnitude, a pulse width, pulse shape, and so on. In some examples, to find this minimum current setting, during initial implant, a clinician may set the pacing output above the patient's native heart rate, so that the chamber of interest (e.g. RV, LV, or atrium) is being paced continuously. The clinician may reduce the pacing amplitude until the pacing pulse no longer causes a contraction, e.g. a loss of capture. In some examples, the capture threshold for a given patient may change over time, e.g. based on the degree of dehydration, taking certain medications, blood sugar levels, and so on. In some examples, IMD 16 may be configured to perform a periodic, e.g. daily or weekly, test for the pacing threshold, for example by decreasing the pacing amplitude to a low setting, and stepping up the pacing amplitude until the electrical current stimulation pulse consistently causes depolarization and a contraction.

In some examples, the most distal electrode 47 may be placed in a phrenic nerve stimulation (PNS) region 35. In some examples distal electrode 47 may be used in combination with one or more other electrodes to sense polarization and depolarization of the left ventricle. Pacing pulses that include electrode 47 may result in stimulation of phrenic nerve 33, which may be uncomfortable for a patient because it may cause undesired contraction of the diaphragm, e.g. hiccups.

The current steering techniques of this disclosure may control specific regions of cardiac tissue that may be stimulated, which in turn may avoid causing stimulation in PNS region 35. It should be understood that the example techniques are not limited to avoiding stimulating in PNS region 35. In some examples, heart 12 may include a necrotic region 34, that may have been caused by cardiac ischemia that has become a myocardial infarction. Although shown near the apex of the right ventricle in the example of FIG. 2A, a necrotic region 34 may occur in many locations on the heart, depending on where blood flow to the heart was reduced or blocked. Necrotic regions, like necrotic region 34, may affect the ability of pacing stimulation pulses to capture the heart muscle and cause a contraction.

The current steering techniques of this disclosure may provide precise current paths through heart tissue to capture the left ventricle such that the left ventricular contraction efficiently pumps blood to the patient's arteries. For example, a contraction that starts near the apex and works toward the anterior portion of the heart may squeeze blood from the left ventricle more efficiently than a contraction that starts in a different location and works toward the apex. The location of the electrodes in LV lead 20 in cardiac vein 37 may provide more precise current paths that require less electrical energy when compared to electrodes placed in other locations, such as locations at a distance from the patient's heart, e.g. subcutaneous, internal thoracic vein, external skin electrodes or other locations.

In operation, a first electrode, e.g. electrode 44 may act as the delivery electrode and a second electrode, e.g. electrode 45, and third electrode, e.g. electrode 46 as the receiving electrodes. In some examples, IMD 16 (not shown in FIG. 2A) may configure electrode 44 to output the electrical current stimulation pulse by connecting the delivery current source to electrode 44. IMB 16 may connect the receiving (e.g. sink) current source to electrodes 45 and 46. In some examples, IMB 16 may cause electrode 44 to output, e.g. deliver, the electrical current stimulation pulse at the same time, e.g., approximately simultaneously, by causing both electrodes 45 and 46 to sink the electrical current stimulation pulse. Therefore, the current path in this example will be from electrode 44 to electrodes 45 and 46.

In other examples, IMD 16 may sequentially activate one or more electrodes. IMB 16 may cause electrode 44 to output the electrical current stimulation pulse simultaneously with causing electrode 46 to sink the electrical current stimulation pulse but pause before activating electrode 45 to also sink the electrical current stimulation pulse. In this manner, IMD 16 may direct the electrical current stimulation pulse through a current path through tissue between electrode 44 and electrode 46, then redirect some electrical energy to a current path between electrode 44 and electrode 45.

In other examples, IMD 16 may, at a first time, configure electrode 44 to output the electrical current stimulation pulse and the RV tip electrode (not shown in FIG. 2A) to sink the electrical current stimulation pulse. At a second time, e.g. within a few milliseconds of the first time, IMB 16 may configure electrode 45 to output the electrical current stimulation pulse and the can of IMD 16 (e.g. housing electrode 4, not shown in FIG. 2A) to sink the electrical current stimulation pulse. In this manner IMB 16, e.g. as configured by a clinician, may sequentially stimulate the LV cardiac tissue in two separate current paths, which for a particular patient, may efficiently capture the LV cardiac tissue and cause the desired depolarization and contraction. In a similar manner, any set of electrodes, e.g. the indifferent electrode, RV coil, RV ring, RA tip, epicardial or other leads not positioned within heart and so on, may be configured to either output or sink the electrical current stimulation pulse to select the desired current path with the desired current amplitude, pulse width, or other parameters to capture the LV cardiac tissue.

Figure 2B:
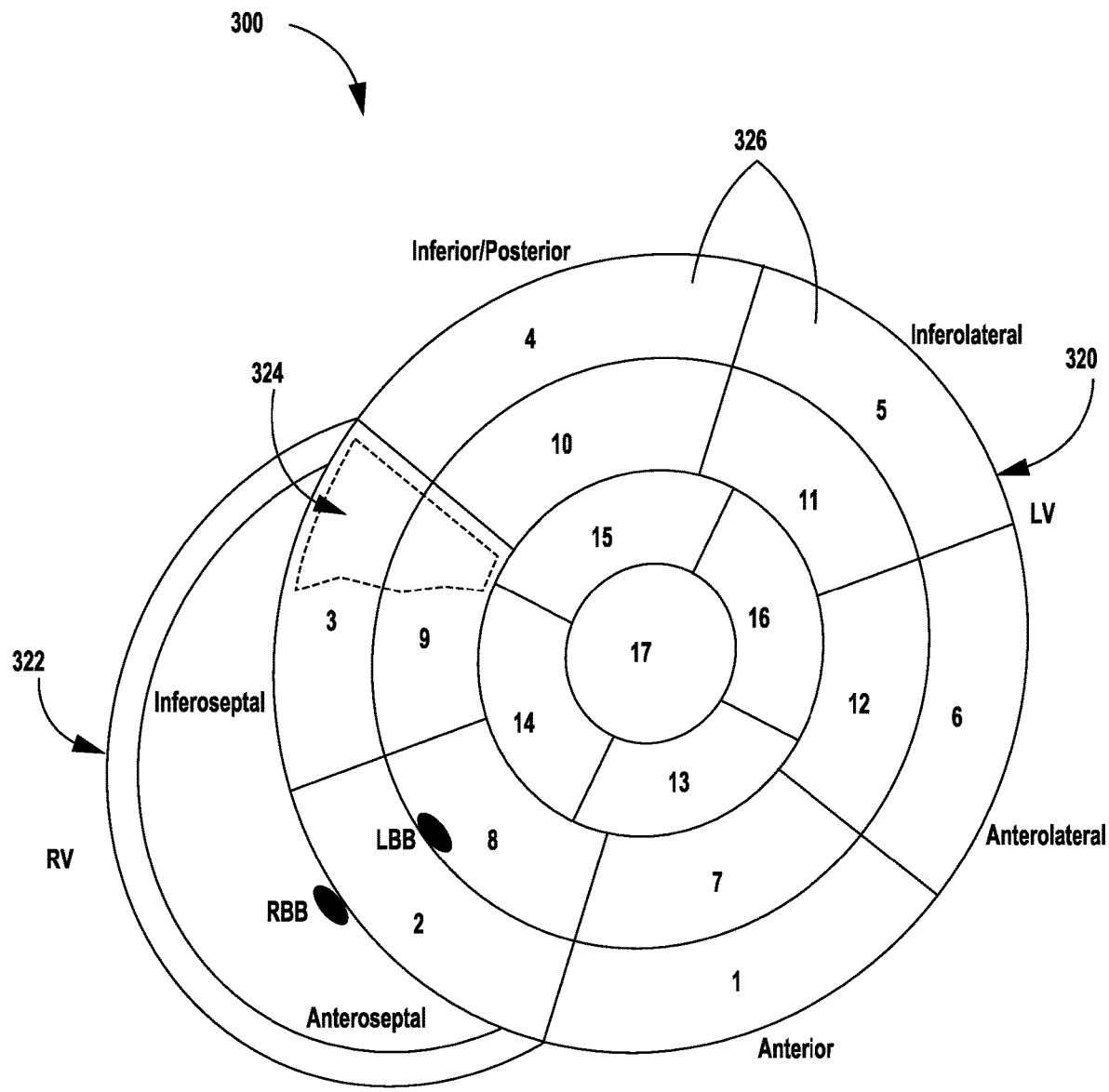
FIG. 2B is a two-dimensional (2D) ventricular map 300 of a patient's heart (e.g., a top-down view) showing the left ventricle 320 in a standard seventeen segment view and the right ventricle 322.

FIG. 2B is a two-dimensional (2D) ventricular map 300 of a patient's heart (e.g., a top-down view) showing the left ventricle 320 in a standard seventeen segment view and the right ventricle 322. Ventricle-from-atrium (VfA) cardiac therapy uses an implantable medical device or system, as shown and described in U.S. Pat. No. 11,058,880 to Yang et al. issued Jul. 13, 2021. The implantable medical device may include a tissue-piercing electrode implanted in the basal and/or septal region of the left ventricular myocardium of the patient's heart from the triangle of Koch region of the right atrium through the right atrial endocardium and central fibrous body. The device may include a right atrial electrode, a right atrial motion detector, or both. The device may be implanted completely within the patient's heart or may use one or more leads to implant electrodes in the patient's heart. The device may be used to provide cardiac therapy, including single or multiple chamber pacing, atrioventricular synchronous pacing, asynchronous pacing, triggered pacing, cardiac resynchronization pacing, tachycardia-related therapy, or conduction system pacing (e.g. left bundle branch pacing, right bundle branch pacing, Bundle of His pacing). A separate medical device may be used to provide some functionality for cardiac therapy, such as sensing, pacing, or shock therapy. Vfa pacing may be combined with the current steering techniques described above in relation to FIGS. 1 and 2A.

The map 300 includes a plurality of areas 326 corresponding to different regions of a human heart. As illustrated, the areas 326 are numerically labeled 1-17 (which, e.g., correspond to a standard 17 segment model of a human heart, correspond to 17 segments of the left ventricle of a human heart, etc.). Areas 326 of the map 300 may include basal anterior area 1, basal anteroseptal area 2, basal inferoseptal area 3, basal inferior area 4, basal inferolateral area 5, basal anterolateral area 6, mid-anterior area 7, mid-anteroseptal area 8, mid-inferoseptal area 9, mid-inferior area 10, mid-inferolateral area 11, mid-anterolateral area 12, apical anterior area 13, apical septal area 14, apical inferior area 15, apical lateral area 16, and apex area 17. The inferoseptal and anteroseptal areas of the right ventricle 322 are also illustrated, as well as the right bunch branch (RBB) and left bundle branch (LBB).

In some embodiments, any of the tissue-piercing electrodes of the present disclosure may be implanted in the basal and/or septal region of the left ventricular myocardium of the patient's heart. In particular, the tissue-piercing electrode may be implanted from the triangle of Koch region of the right atrium through the right atrial endocardium and central fibrous body.

Once implanted, the tissue-piercing electrode may be positioned in the target implant region, such as the basal and/or septal region of the left ventricular myocardium. With reference to map 300, the basal region includes one or more of the basal anterior area 1, basal anteroseptal area 2, basal inferoseptal area 3, basal inferior area 4, mid-anterior area 7, mid-anteroseptal area 8, mid-inferoseptal area 9, and mid-inferior area 10. With reference to map 300, the septal region includes one or more of the basal anteroseptal area 2, basal anteroseptal area 3, mid-anteroseptal area 8, mid-inferoseptal area 9, and apical septal area 14.

In some embodiments, the tissue-piercing electrode may be positioned in the basal septal region of the left ventricular myocardium when implanted. The basal septal region may include one or more of the basal anteroseptal area 2, basal inferoseptal area 3, mid-anteroseptal area 8, and mid-inferoseptal area 9.

In some embodiments, the tissue-piercing electrode may be positioned in the high inferior/posterior basal septal region of the left ventricular myocardium when implanted. The high inferior/posterior basal septal region of the left ventricular myocardium may include a portion of at least one of the basal inferoseptal area 3 and mid-inferoseptal area 9. For example, the high inferior/posterior basal septal region may include region 324 illustrated generally as a dashed-line boundary. As shown, the dashed line boundary represents an approximation of about where the high inferior/posterior basal septal region and may take somewhat different shape or size depending on the particular application. Without being bound by any particular theory, intraventricular synchronous pacing and/or activation may result from stimulating the high septal ventricular myocardium due to functional electrical coupling between the subendocardial Purkinje fibers and the ventricular myocardium.

Figure 3:
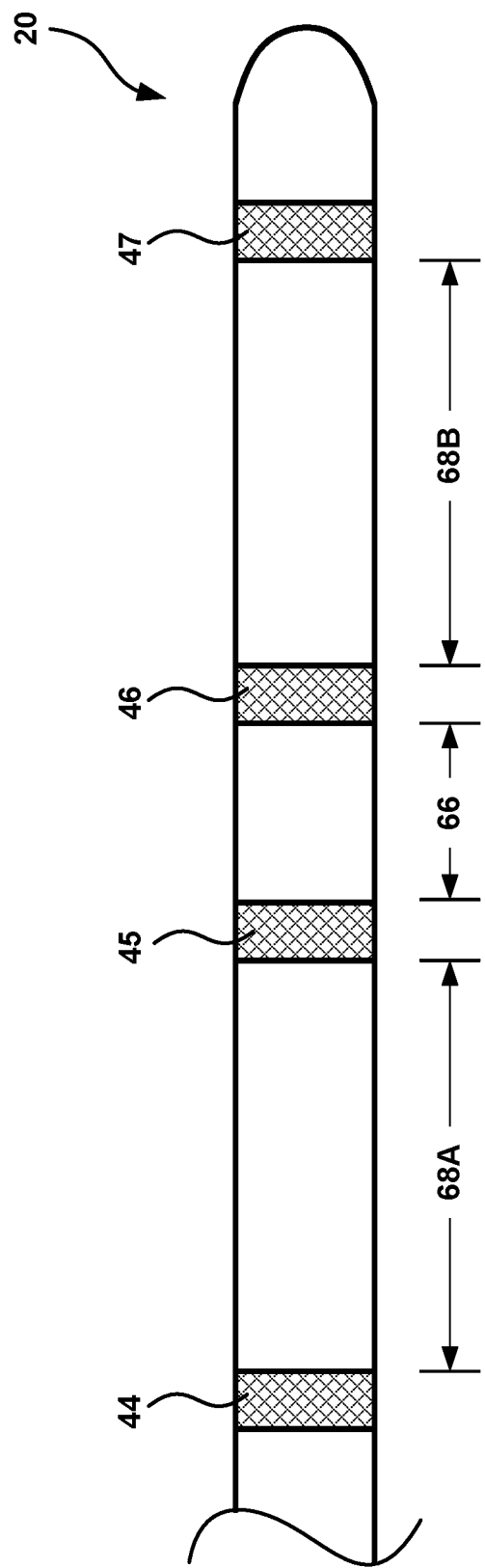
FIG. 3 is a conceptual diagram illustrating an example configuration of a multi-polar cardiac lead.

FIG. 3 is a conceptual diagram illustrating an example configuration of a multi-polar cardiac lead. In the example of FIG. 3, LV lead 20 includes electrodes 44, 45, 46 and 47 located proximate to a distal end of LV lead 20. LV lead 20 includes electrodes 44, 45, 46 and 47 correspond to LV lead 20 and electrodes 44-47 described above in relation to FIGS. 1 and 2. As noted above, though the example of FIG. 3 illustrates a quadripolar lead to simplify the description, LV lead 20 may have any number of electrodes. The distal end of LV lead 20, including electrodes 44, 45, 46 and 47, is configured to be placed in or near LV tissue, e.g., within the coronary sinus or a cardiac vein reachable via the coronary sinus, the right ventricle, in subcutaneous tissue, in the esophagus, or other locations proximal to the heart, as described above in relation to FIG. 2A.

In the example of FIG. 3, electrodes 44 and 45 are separated by an inter-electrode spacing 68A, electrodes 45 and 46 are separate by an inter-electrode spacing 66, and electrodes 46 and 47 are separated by an inter-electrode spacing 68B. Inter-electrode spacings refer to the distance, e.g., measured in a direction substantially parallel to a longitudinal axis of lead 20, from one electrode to another, e.g., center-to-center or edge-to-edge. In some examples, electrodes 45 and 46 may act as a bipolar electrode pair configured to sense a LV bipolar cardiac electrogram signal of tissue of the left ventricle 32 of heart 12 near electrodes 45 and 46. The bipolar electrode pair may be referred to as a short-spacing bipolar electrode pair because of a relatively smaller inter-electrode spacing 66 between electrodes 45 and 46, e.g., relative to a larger inter-electrode spacings 68A and 68B.

In the example of FIG. 3, inter-electrode spacings 68A and 68B (collectively "inter-electrode spacings 68") are relatively larger than inter-electrode spacing 66. Inter-electrode spacings 68 may be the same as, or different than, each other.

The arrangement of electrodes 44-47 and the inter-electrode spacings 66 and 68 illustrated in FIG. 3 are one example. Other example LV leads that may be included in a system according to this disclosure may include a different arrangement of electrodes and inter-electrode spacings. For example, on some LV leads that may be included in a system according to this disclosure, a most proximal pair of electrodes, e.g., electrodes 44 and 45, or a most distal pair of electrodes, e.g., electrode 46 and 47, may have an inter-electrode spacing 66 and act as a bipolar pair of electrodes configured to sense a LV bipolar cardiac electrogram signal of tissue of the left ventricle 32 of heart 12 proximate the bipolar electrode pair. Some LV leads may include a plurality of electrodes having an inter-electrode spacing 66, and thus configured to act as a bipolar pair of electrodes configured to sense a LV bipolar cardiac electrogram signal of tissue of the left ventricle 32 of heart 12 proximate the bipolar electrode pair. IMD 16, described above in relation to FIG. 1, may also be configured to sense LV activity using one or more of LV electrodes 44-47 in conjunction with housing electrode 4, or any other electrode connected to IMD 16 (not shown in FIG. 3). IMD 16 may also be configured to send current-controlled pacing pulses through any combination of electrodes to capture the left ventricle.

In some examples, the current regulated pacing approach of this disclosure may also be applied to other lead configurations and implant locations. For example, IMD 16 may target the His bundle or left bundle branch with a current regulated/steered field from a multiple pole lead (not shown in FIG. 3). Other lead configurations such as a segmented lead may could provide additional field steering ability for cardiac pacing (not shown in FIG. 3).

Figure 4:
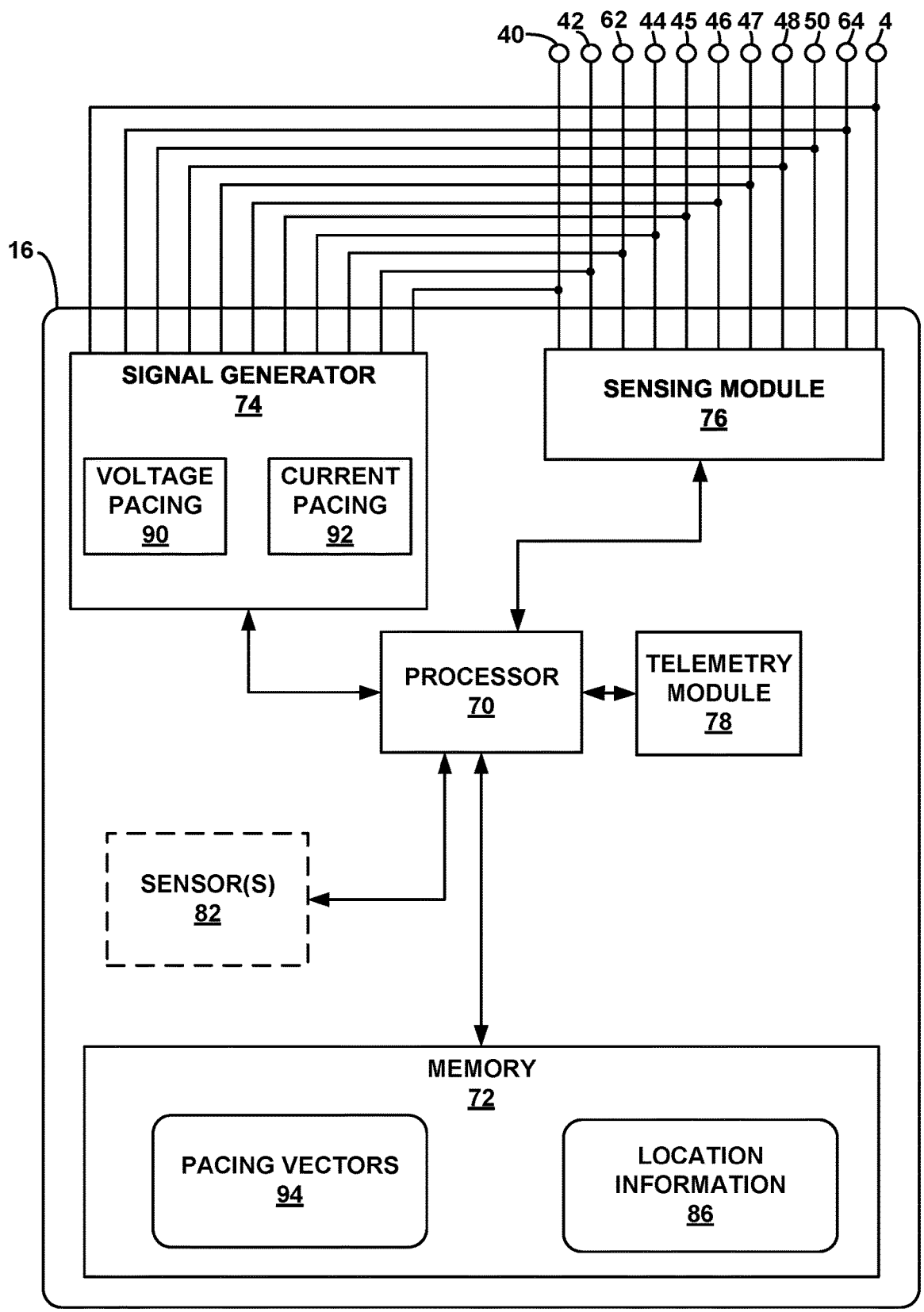
FIG. 4 is a block diagram illustrating an example configuration of an IMD, according to the techniques of this disclosure.

FIG. 4 is a block diagram illustrating an example configuration of an IMD, according to the techniques of this disclosure. IMD 16, leads 44-47, and housing electrode 4 of FIG. 4 correspond to IMD 16, leads 44-47, and housing electrode 4 described above in relation to FIGS. 1-3.

In the example of FIG. 4, IMD 16 includes a processor 70, memory 72, signal generator 74, sensing module 76, telemetry module 78, and one or more sensors 82. Memory 72 may store computer-readable instructions that, when executed by processor 70, cause IMD 16 and processor 70 to perform various functions attributed to IMD 16 and processor 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include processing circuitry such as any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware, or any combination thereof. Generally, processor 70 controls signal generator 74 to deliver stimulation therapy to heart 12 of patient 14 described above in relation to FIG. 1 according to a selected one or more of therapy programs or parameters, which may be stored in memory 72. As an example, processor 70 may control signal generator 74 to deliver electrical pulses with the amplitudes, pulse widths, frequency, or electrode polarities specified by the selected one or more therapy programs or parameters.

Signal generator 74 is configured to generate and deliver electrical stimulation therapy to patient 14. As shown in FIG. 4, signal generator 74 is electrically coupled to electrodes 4, 40, 42, 44-48, 50, 62, and 64, e.g., via conductors of the respective leads 18, 20, and 22 and, in the case of housing electrode 4, within housing 8, described above in relation to FIG. 1. For example, signal generator 74 may deliver pacing, defibrillation or cardioversion pulses to heart 12 via at least two of electrodes 4, 40, 42, 44-48, 50, 62 and 64. In some examples, signal generator 74 delivers stimulation in the form of signals other than pulses such as sine waves, square waves, or other substantially continuous time signals. In some examples, the electrical stimulation therapy may be in the form of voltage-controlled pacing pulses. In other examples, signal generator 74 may also be configured to control which electrodes are configured to output the electrical current stimulation pulse, e.g. current controlled pacing, and which electrodes are configured to sink the electrical current stimulation pulse.

In some examples, signal generator 74 includes a switch module (not shown) and processor 70 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 76 monitors electrical cardiac signals from any combination of electrodes 4, 40, 42, 44-48, 50, 62 and 64. In some examples, sensing module 76 also includes a switch module which processor 70 may control to select which of the available electrodes are used to sense the heart activity, depending upon which electrode combination is used in the current sensing configuration.

As described above in relation to FIGS. 2 and 3, IMD 16 may include current controlled circuitry to deliver electrical current stimulation pulse using current steering techniques. In the example of FIG. 4, signal generator 74 includes voltage pacing circuitry 90 and current pacing circuitry 92. In some examples, processor 70 may control voltage pacing circuitry 90 of signal generator 74 to deliver voltage-controlled pacing pulses via RV lead 18, RA lead 22, housing electrode 4, and/or an indifferent electrode (not shown in FIG. 4). In some examples, processor 70 may control current pacing circuitry 92 of signal generator 74 to deliver current pulses using current steering techniques via one or more electrodes, e.g. electrodes 44-47 of LV lead 20. In some examples, IMD 16 may be configured to deliver only voltage-controlled pacing pulses via RV lead 18 and RA lead 22, and current-controlled pacing pulses via LV lead 20. In other examples, signal generator 74, e.g. using the switch module, may be configured to deliver current controlled pacing stimulation via any combination of electrodes.

In some examples, processor 70 or external computing device 24, described above in relation to FIG. 1, may execute one or more algorithms configured to map responses of the cardiac tissue of heart 12 to current controlled pacing stimulation, e.g. in the form of electrical current stimulation pulses. The one or more algorithms may be stored, for example at memory 72, or a memory device at external computing device 24 and may provide information to a clinician on selecting electrode combinations and electrical current settings, such as amplitude, pulse width etc. that can capture the LV cardiac tissue with the least amount of electrical energy. One example algorithm may include VectorExpress™ LV automated test available from Medtronic, Inc., of Minneapolis, MN VectorExpress is programmer-based algorithm that may allow automated testing of clinician-selected pacing. The clinician may test a variety of LV pacing vectors, then choose the LV pacing vector with the appropriate capture threshold and impedance to ensure capture and maximize device longevity while avoiding phrenic nerve stimulation (PNS). Processor 70 or external computing device 24 may execute similar algorithms. In some examples, IMD 16 may store selected pacing vectors 94 at memory 72.

In some examples, IMD 16 may pace electrode combinations together, e.g., approximately simultaneously. In other examples, IMD 16 may pace electrode combinations in sequence. In other words, some pacing vectors may be stimulated at the same time to capture the desired portion of the left ventricle. In other examples, some pacing vectors may be paced in sequence, e.g., separated in time by an interval. The interval of separation may be fractions of a second.

Sensing module 76 may include one or more detection channels, each of which may comprise an amplifier. The detection channels may be used to sense cardiac signals. Some detection channels may detect events, such as R-waves or P-waves, and provide indications of the occurrences of such events to processor 70. One or more other detection channels may provide the signals to an analog-to-digital converter, for conversion into a digital signal for processing or analysis by processor 70 or external computing device 24.

For example, sensing module 76 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 70 may then use that detection in measuring frequencies of the sensed events.

In some examples, processor 70 may determine whether the patient's heart is contracting as expected based on the sensed events, or lack of a sensed event. For example, IMD 16 may be configured to sense a left ventricular contraction based on sensing whether or not the left ventricle depolarized at the expected time in the cardiac cycle. For example, the left ventricle of patient with a partial left bundle branch block (LBBB) may depolarize at the correct time in the cardiac cycle to indicate a coordinated heart contraction. When the signals from sensing module 76 indicated that the left ventricle fails to depolarize within the expected time window, processor 70 may cause signal generator 74 to deliver an electrical current stimulation pulse between two or more electrodes, based on the programmed configuration for a left ventricular pacing pulse, as described above in relation to FIG. 2A.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 76 includes a wide band channel which may comprise an amplifier with a relatively wider pass band than the narrow band channels. Signals from the electrodes that are selected for coupling to the wide-band amplifier may be converted to multi-bit digital signals by an analog-to-digital converter (ADC) provided by, for example, sensing module 76 or processor 70. Processor 70 may analyze the digitized version of signals from the wide band channel. Processor 70 may employ digital signal analysis techniques to characterize the digitized signals from the wide band channel to, for example, detect and classify the patient's heart rhythm.

Processor 70 may detect and classify the patient's heart rhythm based on the cardiac electrical signals sensed by sensing module 76 employing any of a variety of signal processing methodologies. For example, processor 70 may maintain escape interval counters that may be reset upon sensing of R-waves by sensing module 76. The value of the count present in the escape interval counters when reset by sensed depolarizations may be used by processor 70 to measure the durations of R-R intervals, which are measurements that may be stored in memory 72. Processor 70 may use the count in the interval counters to detect a tachyarrhythmia, such as ventricular fibrillation or ventricular tachycardia. A portion of memory 72 may be configured as a plurality of recirculating buffers, capable of holding series of measured intervals, which may be analyzed by processor 70 to determine whether the patient's heart 12 is presently exhibiting atrial or ventricular tachyarrhythmia.

In some examples, processor 70 may determine that tachyarrhythmia has occurred by identification of shortened R-R interval lengths. In some examples, processor 70 may detect a tachycardia rhythm when the interval length falls below 360 milliseconds (ms) and fibrillation when the interval length falls below 320 ms. These interval lengths are merely examples, and a user may define the interval lengths as desired, which may then be stored within memory 72. In some examples, processor 70 may determine whether the shortened interval length is detected for a certain number of consecutive cycles, for a certain percentage of cycles within a running window, or a running average for a certain number of cardiac cycles.

In some examples, an arrhythmia detection method may include any suitable tachyarrhythmia detection algorithms. In one example, processor 70 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by processor 70 in some examples. For example, EGM morphology may be considered in addition to or instead of interval length for detecting tachyarrhythmias.

In some examples, processor 70 may detect a treatable tachyarrhythmia, such as ventricular fibrillation (VF), based on the EGM, e.g., the R-R intervals and/or morphology (shape) of the EGM, and selects which therapy to deliver via, for example, signal generator 74, to terminate the tachyarrhythmia. An example of therapy may include a defibrillation pulse of a specified magnitude. The detection of the tachyarrhythmia may include a number of phases or steps prior to delivery of the therapy, such as first phase, sometimes referred to as detection, in which a number of consecutive or proximate R-R intervals satisfies a first number of intervals to detect (NID) criterion, a second phase, sometimes referred to as confirmation, in which a number of consecutive or proximate R-R intervals satisfies a second, more restrictive NID criterion. Tachyarrhythmia detection may also include confirmation based on EGM morphology or other sensors subsequent to or during the second phase.

One or more sensors 82 may be optionally included in some examples of IMD 16. Sensor 82 may include one or more accelerometers in some examples. Sensors 82 may additionally or alternatively include other sensors such as a heart sounds sensor, a pressure sensor, a temperature sensor, a flow sensor, or an $O_2$ saturation sensor. In some examples, sensors 82 may detect respiration via one or more electrodes.

Processor 70 may use the information obtained from activity sensor 82 to determine activity level, posture, blood pressure, blood flow, blood oxygen level, or respiratory rate, as examples. In some examples, this information may be used by IMD 16 to aid in the classification of an abnormal heart rhythm. In some examples, this information may be used by IMD 16, or a user of external computing device 24, to determine desired LV pacing locations and timings for delivery of cardiac resynchronization therapy (CRT). For example, blood pressure or flow metrics may indicate the effectiveness LV pacing locations, electrode selection, electrical current polarity, and timings in improving the performance of heart 12.

In some examples, sensors 82 are located outside of the housing 8 of IMD 16. Sensors 82 may be located on a lead that is coupled to IMD 16 or may be implemented in a remote sensor that wirelessly communicates with IMD 16 via telemetry module 78. In any case, sensors 82 are electrically or wirelessly coupled to circuitry contained within housing 8 of IMD 16.

Sensing module 76 may be configured to sense the LV bipolar electrogram signal during LV pacing, e.g., at times when the heart is paced, and depolarizes in response to the pacing rather than intrinsic conduction. Under the control of processor 70, signal generator 74 delivers LV pacing to left ventricle 32 via one or more of the electrodes, e.g., electrode 44 or 47, of LV lead 20, or another implantable LV lead. In some examples, sensing module 76, processor 70, may digitize the LV bipolar electrogram signal.

The locations of the electrodes may be determined using various techniques, such as fluoroscopy or other imaging, or through measuring electrical potentials on the electrodes when exposed to an electrical field, e.g., generated by surface electrodes on patient 14. As examples, the locations of the electrodes may be determined using the LocaLisa® system commercially available from Medtronic, Inc., of Minneapolis, MN, or the EnSite NavX® system commercially available from St. Jude Medical, Inc., of St. Paul, MN Processor 70 may receive such electrode location information, e.g., from such systems, via telemetry module 78. In some examples, electrode location information 86 may be stored at memory 72.

Telemetry module 78 includes any suitable hardware, firmware, software, or any combination thereof for communicating with another device, such as external computing device 24 (FIG. 1). Under the control of processor 70, telemetry module 78 may receive downlink telemetry from and send uplink telemetry to external computing device 24 with the aid of an antenna, which may be internal and/or external. In some examples, processor 70 may transmit cardiac signals, e.g., EGM signals produced by sensing module 76. For example, processor 70 may transmit an LV bipolar cardiac electrogram signal to external computing device 24 or another external computing device via telemetry module 78, e.g., to facilitate analysis of the signal by the external computing device.

Figure 5:
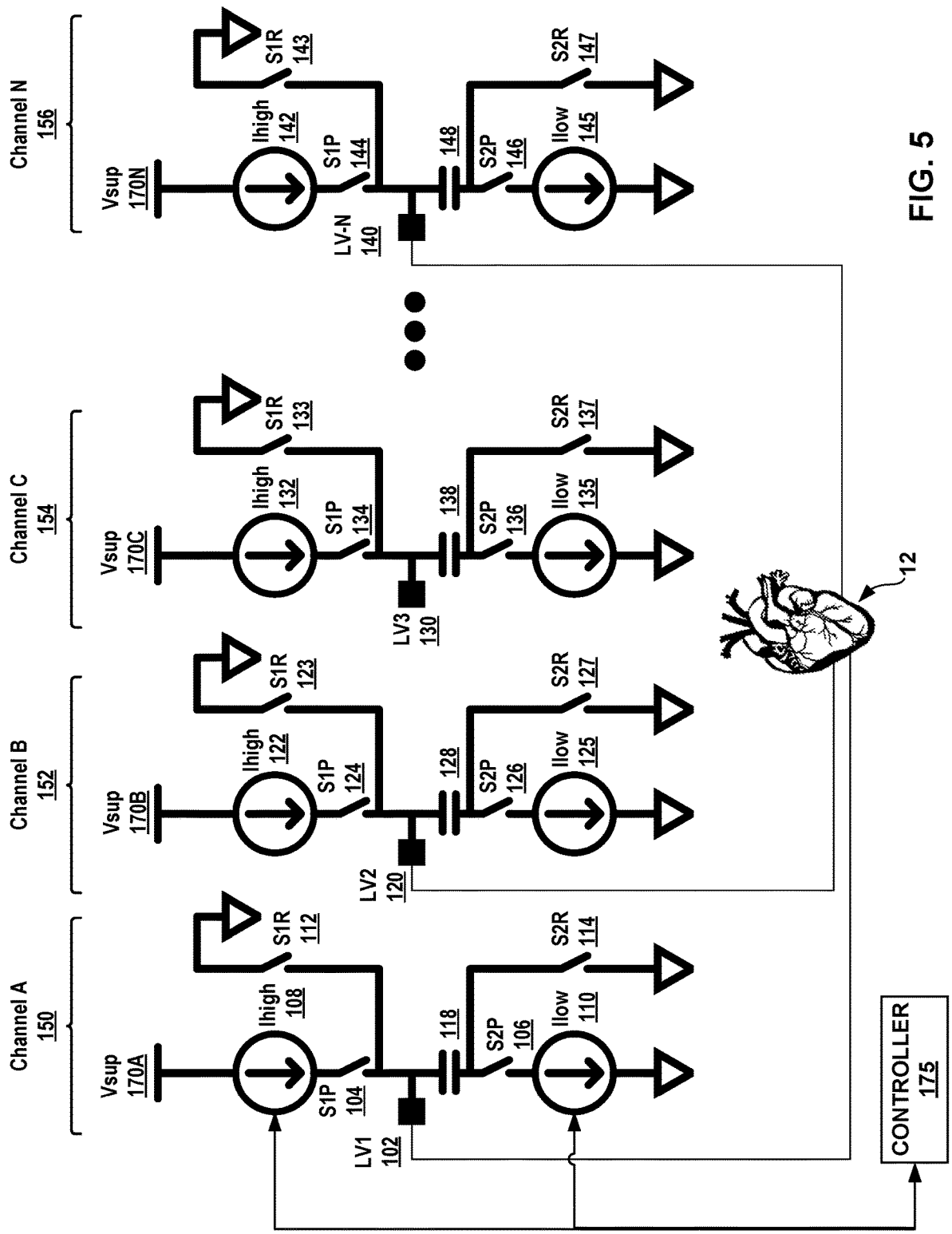
FIG. 5 is a schematic diagram illustrating an example implementation of current-controlled pacing circuitry, according to one or more techniques of this disclosure.

FIG. 5 is a schematic diagram illustrating an example implementation of current-controlled pacing circuitry, according to one or more techniques of this disclosure. The example of FIG. 5 depicts LV pacing channels: channel A 150, channel B 152, channel C 154, and channel N 156. Each of the channels may connect to an electrode of LV lead 20, described above in relation to FIGS. 1-3. For example, LV1 102 may connect to electrode 44, LV2 120 may connect to electrode 45, and so on. Although the example of FIG. 5 only depicts LV electrode channels, in other examples, similar current controlled pacing circuitry may connect to other electrodes of system 10, described above in relation to FIG. 1, such has housing electrode 4 or one or more electrodes of RV lead 18 (not shown in FIG. 5). In some examples, IMD 16 may be configured to connect either current controlled pacing circuitry or voltage-controlled pacing circuitry to an electrode of system 10, e.g. via a switching network. In some examples the IMD may be configured to bypass the current regulation portion of the circuit and deliver voltage controlled electrical stimulation pulses, e.g. generated by voltage pacing circuitry 90 of signal generator 74 includes as described above in relation to FIG. 4. Current pacing circuitry 92, described above in relation to FIG. 4, may correspond to channels A-N depicted in FIG. 5.

FIG. 5 also includes controller 175, which is shown as operatively coupled to current sources Ihigh 108 and Ilow 110. However, controller 175 may be considered as operatively coupled to each of the current sources, as well as all the switches in FIG. 5, though only shown connected to current sources Ihigh 108 and Ilow 110 to simplify FIG. 5. In some examples, controller 175 may also receive indications from a current source or a switch of FIG. 5, such as switch status (open or closed), temperature of the current source, or some other status or indicator from the current source.

Controller 175 may configure each current source according to programmed pacing settings, which may be set up by the clinician during an initial implant of a medical device, such as IMD 16 described above in relation to FIGS. 1 and 4. Programmed pacing settings may include current pulse amplitude, pulse width, pulse shape, electrode configuration and other settings. In the example of FIG. 5, controller 175 may correspond to a combination of processor 70 and signal generator 74, described above in relation to FIG. 4, but shown as a single block to simplify FIG. 5.

For channel A 150, in the example of FIG. 5, input voltage from a pacing power supply of IMD 16, Vsup 170A, connects to an input terminal of a first current source, Ihigh 108. The output terminal of Ihigh 108 connects to electrode LV1 102 via a lead, such as LV lead 20 through switch S1P 104. Electrode LV1 102 also connects to ground through recharge switch S1R 112 and to switch S2P 106 and recharge switch S2R 114 through capacitor 118. Recharge switch S2R 114 connects to a reference voltage level, shown as ground in the example of FIG. 5. Switch S2P 106 connects capacitor 118 to an input terminal of current source Ilow 110 and the output terminal of current source Ilow 110 connects to the same reference voltage level, which is shown as ground in FIG. 5.

The circuit arrangement in the example of FIG. 5 is just one example implementation of a current controlled pacing source. In other examples, the recharge switches, e.g. recharge switch S1R 112 and S2R 114 may be replaced with current sources. In some examples, the circuits of each channel may have additional blocking capacitors or other components. As described above in relation to FIGS. 1-4, IMD 16 may include any number of channels that drive any number of electrodes on LV lead 20.

In other examples, the circuit arrangement of FIG. 5 may include more or fewer components. For example, channel A 150 may include one or more additional switches, not shown in FIG. 5, between electrode LV1 102 and capacitor 118 to isolate the current controlled circuitry in examples in which an IMD is programmed to deliver voltage controlled pacing pulses through electrode LV1 102. In some examples, an IMD, such as IMD 16 may be configured to deliver current controlled electrical current stimulation pulses via an electrode such as electrode LV1 102 at a first time and deliver a voltage controlled pulse via electrode LV1 102 at a second time.

For channel B 152, the input voltage from the pacing power supply, Vsup 170B connects to an input terminal of current source, Ihigh 122. The output terminal of Ihigh 122 connects to electrode LV2 120 via a lead through switch S1P 124. Electrode LV2 120 also connects to ground through recharge switch S1R 123 as well as to switch S2P 126 and recharge switch S2R 127 through capacitor 128. Recharge switch S2R 127 connects to the reference voltage level, shown as ground. Switch S2P 126 connects capacitor 128 to an input terminal of current source Ilow 125 and the output terminal of current source Ilow 125 connects to ground.

For channel C 154, the input voltage from the pacing power supply, Vsup 170C connects to an input terminal of current source, Ihigh 132. The output terminal of Ihigh 132 connects to electrode LV3 130 via a lead through switch S1P 134. Electrode LV3 130 also connects to ground through recharge switch S1R 133 as well as to switch S2P 136 and recharge switch S2R 137 through capacitor 138. Recharge switch S2R 137 connects to the reference voltage level, shown as ground. Switch S2P 136 connects capacitor 138 to an input terminal of current source Ilow 135 and the output terminal of current source Ilow 135 connects to ground.

For channel N 156, the input voltage from the pacing power supply, Vsup 170N connects to an input terminal of current source, Ihigh 142. The output terminal of Ihigh 142 connects to electrode LV3 140 via a lead through switch S1P 144. Electrode LV3 140 also connects to ground through recharge switch S1R 143 as well as to switch S2P 146 and recharge switch S2R 147 through capacitor 148. Recharge switch S2R 147 connects to the reference voltage level, shown as ground. Switch S2P 146 connects capacitor 148 to an input terminal of current source Ilow 145 and the output terminal of current source Ilow 145 connects to ground. In some examples Vsup 170A-170N may have the same magnitude. In other examples, each of Vsup 170A-170N may be configured with a different voltage magnitude.

In operation, as described above in relation to FIG. 4, processing circuitry of controller 175, such as processor 70, may control current pacing circuitry 92 of signal generator 74, e.g. any one or more of channels A 152 to channel N 156. In the example of FIG. 5, channel N 156 is selected as the delivery, or high side channel. Channels A 150 and B 152 are selected as the receiving or low side channels. In this manner, TMD 16 may steer current to apply a stimulation pulse to only selected tissue of heart 12, e.g. as selected by a clinician for a particular patient's condition and anatomy.

Controller 175 may configure the selected current sources to output or sink the electrical current stimulation pulse according to the programmed pacing settings. For example, as described above in relation to FIG. 4, processor 70 may retrieve the programmed pacing settings from memory 72, which may include a current amplitude, pulse width, and other settings, and cause Thigh 142 to generate a current-controlled pacing pulse according to the settings. Controller 175 may close switch S1P 144 at the appropriate time, based on, for example, the timing of other pacing pulses delivered through RA lead 22 and RV lead 18, or based on measured activity of heart 12 sensed by sensing module 76.

Controller 175 may cause switches S2P 125 and S2P 106 to close and set Ilow 110 and Ilow 125 to receive a portion of the energy delivered by Ihigh 142. In some examples, Ilow 110 and Ilow 125 may be configured to receive half of the current delivered by Ihigh 142. In other examples, Ilow 110 and Ilow 125 may be configured to receive an unequal portion of the current to steer the current through the desired cardiac tissue. In other words, the various current sources and sinks of this disclosure are regulated (e.g. controlled). The regulated current sources and sinks forces the current to specifically split and/or combine between the electrodes, e.g. current steering. For example, Ilow 110 may be configured to receive 60% of the delivered current and Ilow 125 may be configured to receive 40% of the current delivered by Ihigh 142. In other examples, current may be split among other electrodes, e.g. 50/25/25, or any other desired current split. In some examples, controller 175 may control the circuitry of FIG. 5 to deliver a biphasic pacing pulse, e.g. by delivering a first portion of the pulse in a first direction and a second portion of the pulse in a second direction.

Figure 6:
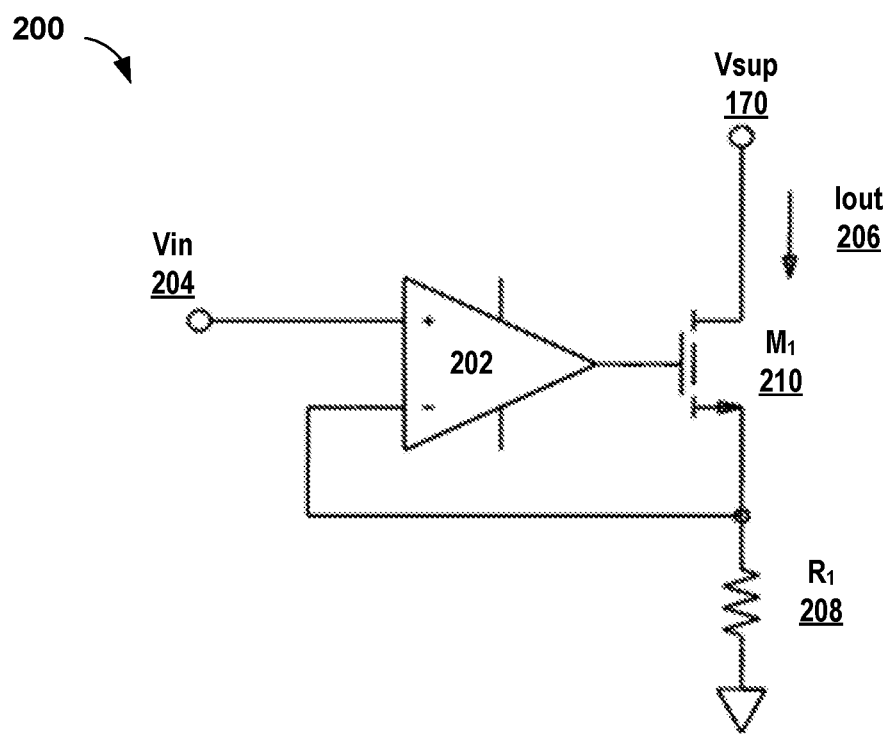
FIG. 6 is a schematic diagram illustrating an example implementation of a current source according to one or more techniques of this disclosure.

FIG. 6 is a schematic diagram illustrating an example implementation of a current source according to one or more techniques of this disclosure. Circuit 200 may correspond to any of Ihigh 108-142 and Ilow 110-145 described above in relation to FIG. 5. Circuit 200 may also replace any of recharge switches S1R 112-133 or S2R 114-147 to provide current steering for the recharge portion of the pacing cycle. In other examples, a different configuration of a current regulation circuit may correspond to Ihigh 108-142 and Ilow 110-145.

Circuit 200, in the example of FIG. 6, is voltage to current conversion circuit using source degeneration on a metal oxide semiconductor field effect transistor (MOSFET). The drain of N-channel transistor M1 210 connects to a supply voltage, Vsup 170, which may correspond to Vsup 170 described above in relation to FIG. 4. Resistor R1 208 provides source degeneration by connecting the source of transistor M1 210 to a reference voltage, such as ground. The output of amplifier 202 connects to the gate of transistor M1 210 to control the magnitude and duration of Tout 206. Processor 70 controls Tout 206 by controlling input voltage Vin 204, which is connected to the non-inverting input of amplifier 202. The inverting input connects to the source of transistor 210. Processor 70 may control current pulse amplitude, pulse width, pulse shape, e.g., an increasing pulse, a decaying pulse or other pulse shape or other aspects of the stimulation therapy delivered to the cardiac tissue.

Figure 7:
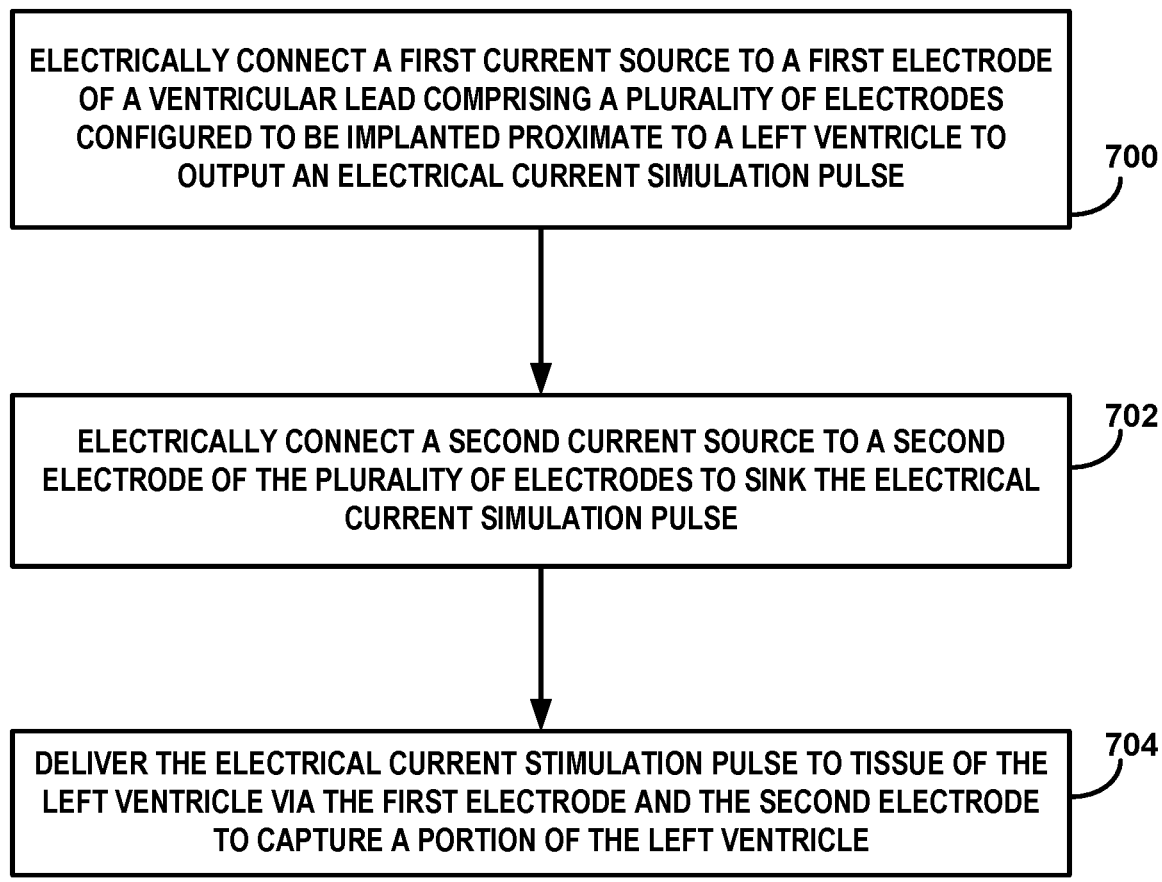
FIG. 7 is a flow chart illustrating an example mode of operation of the medical system of this disclosure.

FIG. 7 is a flow chart illustrating an example mode of operation of the medical system of this disclosure. The blocks of FIG. 7 will be described in terms of FIGS. 1-5.

Processing circuitry, such as processor 70, depicted in FIG. 4, may cause a first current source to electrically connect to a first electrode of a ventricular lead comprising a plurality of electrodes. The ventricular lead may be configured to be implanted proximate to a left ventricle to output an electrical current simulation pulse (700). As described above in relation to FIG. 5, signal generator 74 may close switch S1P 144 to electrically connect Ihigh 142 to electrode LV-N 140. In other examples, signal generator 74 may electrically connect a current source to an electrode separate from the electrodes on LV lead 20, e.g. housing electrode 4, an electrode on a lead extension, or some other electrode.

In some examples, processing circuitry 20, may configure settings for the first current source to output the electrical current stimulation pulse. For example, processing circuitry 70 may adjust the voltage of Vsup 170, shown in FIGS. 5 and 6 and configure any control circuitry for Vin 204 to output an electrical current stimulation current pulse with a selected amplitude, pulse shape, pulse width and other characteristics. Processing circuitry 70 may select the first current source, e.g. any of current sources Ihigh 108-142 based on the desired pacing vector, e.g. as set by a clinician during the implant procedure for IMD 16, or later office visit. For example, the clinician may set the pacing vector to avoid a necrotic region, e.g. necrotic region 34, or to avoid stimulating phrenic nerve 33, as described above in relation to FIG. 2A. In other examples, the clinician may place LV lead 20 to capture other tissue of heart 12, such as the bundle of His or other portions of the bundle branches, Purkinje fibers, or other cardiac tissue to deliver a current-controlled pacing pulse and capture the left ventricle.

In other examples, the current steering techniques of this disclosure may deliver electrical stimulation therapy to, for example, atrial tissue, the right ventricle, or other cardiac tissue. In other words, the techniques of this disclosure may include the ability to stimulate various portions of the heart and from various intra- and extra-cardiac locations, as described above in relation to FIG. 1. For example, a multiple electrode lead in the right ventricle may be configured to steer current towards the Bundle of His. In some examples, pacing stimulations from this location may provide an improved physiologic cardiac response than traditional right ventricle apex pacing. In other examples, the techniques of this disclosure may steer pacing current to cardiac tissue from electrode placements, such as temporary pacing from a lead placed in the esophagus to provide pacing and avoid unwanted nerve stimulation.

Processor 70 may cause signal generator 74 to electrically connect the other one or more current sources to the associated electrode (702). For example, signal generator 74 may close switch S2P 126 to electrically connect Ilow 125 to electrode LV2 120, e.g. through capacitor 128. In this manner, medical system 10 may deliver the electrical current stimulation pulse to tissue of the left ventricle via at least the first electrode and the second electrode to capture, e.g., cause depolarization of, a portion of the left ventricle (704).

As described above in relation to FIG. 5, processor 70 may configure one or more additional current sources to sink the electrical current stimulation pulse. In the example of a single current source, the second current source may be configured to receive all of the electrical energy delivered in the electrical current stimulation pulse. In the example of multiple current sources, the current sources may be configured to receive a portion of the electrical current stimulation pulse such that the stimulation pulse travels through the desired cardiac tissue using current steering.

In this manner the techniques of this disclosure provide advantages that those skilled in the art may not have appreciated. As described above in relation to FIG. 5, current steering techniques using a plurality of electrodes, including electrodes in contact with left ventricular cardiac tissue, may provide more precise control of electrical stimulation pulses, when compared to other techniques. The more precise control may also provide an advantage in requiring less electrical energy in each pulse to reach the capture threshold for the target tissue and thus may extend the battery life for a device. By applying precise control to cardiac pacing, the techniques of this disclosure may provide a solution to a long-felt, but unsolved need.

The current steering techniques of this disclosure applied to left ventricular chamber pacing may represent an incremental improvement in a crowded art field. Incremental improvements may serve the public interest, e.g. in the example of this disclosure may result in improved coordinated contraction of a patient's heart, which may lead to more efficient blood flow. Also, reduced battery consumption and longer battery life may result in fewer surgeries for a patient to replace a device, and therefore reduced risk of infection or complications. For a rechargeable device, longer battery life may result in improved quality of life for a patient by reducing the amount of time spent recharging the device. In addition, current steering techniques applied to cardiac pacing, may not have been implemented, despite the advantages, which may indicate that the techniques of this disclosure may not have been obvious to those skilled in the art.

In one or more examples, the functions described above may be implemented in hardware, software, firmware, or any combination thereof. For example, the various components of FIGS. 1 and 2, such as controller 102, ECS controller 202 and ADC 104 may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

The term "non-transitory" may indicate that the storage medium is not embodied in a carrier wave or a propagated signal. In certain examples, a non-transitory storage medium may store data that can, over time, change (e.g., in RAM or cache). By way of example, and not limitation, such computer-readable storage media, may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Combinations of the above should also be included within the scope of computer-readable media.

Instructions may be executed by one or more processors, such as one or more DSPs, general purpose microprocessors, ASICs, FPGAs, or other equivalent integrated or discrete logic circuitry. Accordingly, the term "processor," as used herein, such as ECS controller 202, may refer to any of the foregoing structure or any other structure suitable for implementation of the techniques described herein. Also, the techniques could be fully implemented in one or more circuits or logic elements.

The techniques of this disclosure may be implemented in a wide variety of devices or apparatuses, including, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

The techniques of this disclosure may also be described in the following examples.

Example 1: A medical system comprising: an implantable medical device coupled to a cardiac lead and configured to deliver pacing therapy to cardiac tissue of a heart via a plurality of electrodes of the cardiac lead, wherein the implantable medical device comprises a first current source configured to output an electrical current stimulation pulse and a second current source configured to sink the electrical current stimulation pulse to capture a portion of the cardiac tissue; and processing circuitry configured to: electrically connect the first current source to a first electrode of the plurality of electrodes to output the electrical current stimulation pulse to the cardiac tissue; and electrically connect the second current source to a second electrode of the plurality of electrodes to sink the electrical current stimulation pulse to the cardiac tissue.

Example 2: The medical system of example 1, wherein the implantable medical device further comprises a third current source configured to sink the electrical current stimulation pulse, and wherein the processing circuitry is further configured to: electrically connect the third current source to a third electrode of the plurality of electrodes to sink the electrical current stimulation pulse to the cardiac tissue, such that the electrical current stimulation pulse captures the portion of the cardiac tissue between the first electrode and the second and the third electrodes.

Example 3: The medical system of example 1, wherein the implantable medical device further comprises a third current source configured to output the electrical current stimulation pulse, and wherein the processing circuitry is further configured to electrically connect the third current source to a third electrode of the plurality of electrodes to output the electrical current stimulation pulse to the cardiac tissue, such that the electrical current stimulation pulse captures the portion of the cardiac tissue between the third electrode and the second and the first electrodes.

Example 4: The medical system of example 1, wherein the implantable medical device further comprises a third current source configured to sink the electrical current stimulation pulse, and wherein the processing circuitry is further configured to: electrically connect the third current source to a third electrode to sink the electrical current stimulation pulse to the cardiac tissue, wherein the third electrode is separate from the plurality of electrodes, such that the electrical current stimulation pulse passes through a portion of the cardiac tissue between the first electrode to the second electrode and the third electrode.

Example 5: The medical system example 4, wherein the third electrode is a housing electrode proximate to a housing of the implantable medical device.

Example 6: The medical system of any combination of examples 1, 4 and 5, wherein the third electrode is a part of a second lead separate from the cardiac lead electrode and the second lead is electrically connected to the implantable medical device.

Example 7: The medical system of example 1, wherein the implantable medical device further comprises a third current source configured to output the electrical current stimulation pulse, and wherein the processing circuitry is further configured to: electrically connect a third current source to a third electrode to output the electrical current stimulation pulse to the cardiac tissue, wherein the third electrode is separate from the plurality of electrodes, such that the electrical current stimulation pulse passes through a portion of the cardiac tissue between the third electrode to the second electrode and the first electrode.

Example 8: The medical system of example 7, wherein the third electrode is a housing electrode proximate to a housing of the implantable medical device.

Example 9: The medical system of any combination of examples 1, 7 and 8, wherein the third electrode is a part of a second lead separate from the cardiac lead and the second lead is electrically connected to the implantable medical device.

Example 10: The medical system of example 1, wherein the cardiac tissue comprises a left ventricle of the heart.

Example 11: The medical system of example 1, wherein the cardiac tissue comprises one or more of: a right atrium, a right ventricle, Purkinje fibers, bundle of His, and a bundle branch.

Example 12: A method comprising: electrically connecting a first current source to a first electrode of a cardiac lead comprising a plurality of electrodes configured to be implanted proximate to a cardiac tissue to output an electrical current stimulation pulse; electrically connecting a second current source to a second electrode of the plurality of electrodes to sink the electrical current stimulation pulse; and delivering the electrical current stimulation pulse to tissue of the cardiac tissue via the first electrode and the second electrode to capture a portion of the cardiac tissue.

Example 13: The method of example 12, further comprising: electrically connecting a third current source to a third electrode of the plurality of electrodes, configured to sink the electrical stimulation pulse; and delivering the electrical current stimulation pulse to tissue of the cardiac tissue such that the electrical current stimulation pulse passes through a portion of the cardiac tissue between the first electrode to the second electrode and the third electrode.

Example 14: The method of example 12, further comprising: electrically connecting a third current source to a third electrode of the plurality of electrodes, configured to output the electrical current stimulation pulse; and delivering the electrical current stimulation pulse to tissue of the cardiac tissue such that the electrical current stimulation pulse passes through a portion of the cardiac tissue between the third electrode to the second electrode and the first electrode.

Example 15: The method of example 12, further comprising: electrically connecting a third current source to a third electrode configured to sink the electrical current stimulation pulse, wherein the third electrode is separate from the plurality of electrodes, delivering the electrical current stimulation pulse to tissue of the cardiac tissue such that the electrical current stimulation pulse passes through a portion of the cardiac tissue between the first electrode to the second electrode and the third electrode.

Example 16: The method of example 15, wherein the third electrode is a housing electrode proximate to a housing of an implantable medical device electrically connected to the cardiac lead.

Example 17: The method of any combination of examples 12, 15, and 16, wherein the third electrode is a part of a second lead separate from the cardiac lead, and the second lead and the cardiac lead are electrically connected to an implantable medical device.

Example 18: The method of example 12, further comprising: electrically connecting a third current source to a third electrode configured to output the electrical stimulation pulse, wherein the third electrode is separate from the plurality of electrodes; and delivering the electrical current stimulation pulse to tissue of the cardiac tissue such that the electrical current stimulation pulse passes through a portion of the cardiac tissue between the third electrode to the second electrode and the first electrode.

Example 19: The method of example 16, wherein the third electrode is a housing electrode proximate to a housing of an implantable medical device electrically connected to the cardiac lead.

Example 20: The method of any combination of examples 12, 18, and 19, wherein the third electrode is a part of a second lead separate from the cardiac lead, and wherein the second lead and the cardiac lead are electrically connected to an implantable medical device.

Example 21: The method of example 12, wherein the cardiac tissue comprises a left ventricle of the heart.

Example 22: The method of example 12, wherein the cardiac tissue comprises one or more of: a right atrium, a right ventricle, Purkinje fibers, bundle of His, and a bundle branch.

Example 23: A computer readable storage medium containing instructions that when executed by processing circuitry of an implantable medical device, cause the processing circuitry to: electrically connect a first current source to a first electrode of a plurality of electrodes to output an electrical current stimulation pulse to a cardiac tissue; and electrically connect a second current source to a second electrode of the plurality of electrodes to sink the electrical current stimulation pulse, wherein a cardiac lead comprising the plurality of electrodes is coupled to the implantable medical device, wherein the implantable medical device is configured to deliver pacing therapy to the cardiac tissue of a heart via the plurality of electrodes of the cardiac lead, wherein the implantable medical device comprises the first current source configured to output an electrical current stimulation pulse and the second current source configured to sink the electrical current stimulation pulse to capture a portion of the cardiac tissue.

Example 24: The computer readable storage medium of example 23, wherein the implantable medical device further comprises a third current source configured to sink the electrical current stimulation pulse, and wherein instructions further cause the processing circuitry to electrically connect the third current source to a third electrode of the plurality of electrodes to sink the electrical current stimulation pulse to the cardiac tissue, such that the electrical current stimulation pulse captures the portion of the cardiac tissue between the first electrode and the second and the third electrodes.

Example 25: The computer readable storage medium of claim 23, wherein the implantable medical device further comprises a third current source configured to output the electrical current stimulation pulse, and wherein the processing circuitry is further configured to electrically connect the third current source to a third electrode of the plurality of electrodes to output the electrical current stimulation pulse to the cardiac tissue, such that the electrical current stimulation pulse captures the portion of the cardiac tissue between the third electrode and the second and the first electrodes.

Example 26: The computer readable storage medium of claim 23, wherein the cardiac tissue comprises a left ventricle of the heart.

Example 27: The computer readable storage medium of claim 23, wherein the cardiac tissue comprises one or more of: a right atrium, a right ventricle, Purkinje fibers, bundle of His, and a bundle branch.

Example 28: A medical device comprising: means for electrically connecting a first current source to a first electrode of a cardiac lead comprising a plurality of electrodes configured to be implanted proximate to a cardiac tissue to output an electrical current stimulation pulse; means for electrically connecting a second current source to a second electrode of the plurality of electrodes to sink the electrical current stimulation pulse; and a means for delivering the electrical current stimulation pulse to tissue of the cardiac tissue via the first electrode and the second electrode to capture a portion of the cardiac tissue.

Example 29: The medical device of example 22, further comprising: means for electrically connecting a third current source to a third electrode of the plurality of electrodes, configured to sink the electrical stimulation pulse; and means for delivering the electrical current stimulation pulse to tissue of the cardiac tissue such that the electrical current stimulation pulse passes through a portion of the cardiac tissue between the first electrode to the second electrode and the third electrode.

Example 30: The medical device of example 28, further comprising: means for electrically connecting a third current source to a third electrode of the plurality of electrodes, configured to output the electrical current stimulation pulse; and means for delivering the electrical current stimulation pulse to tissue of the cardiac tissue such that the electrical current stimulation pulse passes through a portion of the cardiac tissue between the third electrode to the second electrode and the first electrode.

Example 31: The medical device of example 28, further comprising: means for electrically connecting a third current source to a third electrode configured to sink the electrical current stimulation pulse, wherein the third electrode is separate from the plurality of electrodes; and means for delivering the electrical current stimulation pulse to tissue of the cardiac tissue such that the electrical current stimulation pulse passes through a portion of the cardiac tissue between the first electrode to the second electrode and the third electrode.

Example 32: The medical device of example 31, wherein the third electrode is a housing electrode proximate to a housing of an implantable medical device electrically connected to the cardiac lead.

Example 33: The medical device of example 31, wherein the third electrode is a part of a second lead separate from the cardiac lead electrode, and wherein the second lead and the cardiac lead are electrically connected to an implantable medical device.

Example 34: The medical device of example 29, further comprising: means for electrically connecting a third current source to a third electrode configured to output the electrical stimulation pulse, wherein the third electrode is separate from the plurality of electrodes; and means for delivering the electrical current stimulation pulse to tissue of the cardiac tissue such that the electrical current stimulation pulse passes through a portion of the cardiac tissue between the third electrode to the second electrode and the first electrode.

Example 35: The medical device of example 34, wherein the third electrode is a housing electrode proximate to a housing of an implantable medical device electrically connected to the cardiac lead.

Example 36: The medical device of example 35, wherein the third electrode is a part of a second lead separate from the cardiac lead electrode, and wherein the second lead and the cardiac lead are electrically connected to an implantable medical device.

Example 37: The medical device of claim 28, wherein the cardiac tissue comprises a left ventricle of the heart.

Example 38: The medical device of claim 28, wherein the cardiac tissue comprises one or more of: a right atrium, a right ventricle, Purkinje fibers, bundle of His, and a bundle branch.

Example 39. The medical system of example 1, wherein a first channel of implantable medical device comprises the first current source, the first channel further comprising: a first switch configured to connect an output terminal of the first current source to the first electrode; a first recharge switch configured to connect the first electrode to a reference voltage; a second recharge switch configured to connect the first electrode to the reference voltage through a capacitor; a second current source, comprising an input terminal and an output terminal wherein: the output terminal of the second current source connects to the reference voltage, the input terminal of the second current source is configured to connect to the first electrode through the capacitor and a second switch, the second current source is configured to sink current from the first electrode when the second switch is closed and conducting current.

Various examples of the disclosure have been described. These and other examples are within the scope of the following claims.

What is claimed is:

1. A medical system comprising:
an implantable medical device coupled to a cardiac lead and configured to deliver pacing therapy to cardiac tissue of a heart via a plurality of electrodes of the cardiac lead, wherein the implantable medical device comprises a first current source configured to output an electrical current stimulation pulse and a second current source configured to sink the electrical current stimulation pulse to capture a portion of the cardiac tissue; and processing circuitry configured to:
electrically connect the first current source to a first electrode of the plurality of electrodes to output the electrical current stimulation pulse to the cardiac tissue; and
electrically connect the second current source to a second electrode of the plurality of electrodes to sink the electrical current stimulation pulse to the cardiac tissue,
wherein a first channel of implantable medical device comprises the first current source, the first channel further comprising:
a first switch configured to connect an output terminal of the first current source to the first electrode;
a first recharge switch configured to connect the first electrode to a reference voltage;
a second recharge switch configured to connect the first electrode to the reference voltage through a capacitor; and
a second first channel current source, comprising an input terminal and an output terminal wherein:
the output terminal of the second first channel current source connects to the reference voltage,
the input terminal of the second first channel current source is configured to connect to the first electrode through the capacitor and a second switch, and
the second first channel current source is configured to sink current from the first electrode when the second switch is closed and conducting current.

2. The medical system of claim 1,
wherein the implantable medical device further comprises a third current source configured to sink the electrical current stimulation pulse, and
wherein the processing circuitry is further configured to:
electrically connect the third current source to a third electrode of the plurality of electrodes to sink the electrical current stimulation pulse to the cardiac tissue, such that the electrical current stimulation pulse captures the portion of the cardiac tissue between the first electrode and the second and the third electrodes.

3. The medical system of claim 1,
wherein the implantable medical device further comprises a third current source configured to output the electrical current stimulation pulse, and
wherein the processing circuitry is further configured to electrically connect the third current source to a third electrode of the plurality of electrodes to output the electrical current stimulation pulse to the cardiac tissue, such that the electrical current stimulation pulse captures the portion of the cardiac tissue between the third electrode and the second and the first electrodes.

4. The medical system of claim 1,
wherein the implantable medical device further comprises a third current source configured to sink the electrical current stimulation pulse, and
wherein the processing circuitry is further configured to:
electrically connect the third current source to a third electrode to sink the electrical current stimulation pulse to the cardiac tissue, wherein the third electrode is separate from the plurality of electrodes, such that the electrical current stimulation pulse passes through a portion of the cardiac tissue between the first electrode to the second electrode and the third electrode.

5. The medical system of claim 4, wherein the third electrode is a housing electrode proximate to a housing of the implantable medical device.

6. The medical system of claim 5, wherein the third electrode is a part of a second lead separate from the cardiac lead electrode and the second lead is electrically connected to the implantable medical device.

7. The medical system of claim 1,
wherein the implantable medical device further comprises a third current source configured to output the electrical current stimulation pulse, and
wherein the processing circuitry is further configured to:
electrically connect a third current source to a third electrode to output the electrical current stimulation pulse to the cardiac tissue, wherein the third electrode is separate from the plurality of electrodes, such that the electrical current stimulation pulse passes through a portion of the cardiac tissue between the third electrode to the second electrode and the first electrode.

8. The medical system of claim 7, wherein the third electrode is a housing electrode proximate to a housing of the implantable medical device.

9. The medical system of claim 8, wherein the third electrode is a part of a second lead separate from the cardiac lead and the second lead is electrically connected to the implantable medical device.

10. The medical system of claim 1, wherein the cardiac tissue comprises a left ventricle of the heart.

11. The medical system of claim 1, wherein the cardiac tissue comprises one or more of: a right atrium, a right ventricle, Purkinje fibers, bundle of His, and a bundle branch.

12. A computer readable storage medium containing instructions that when executed by processing circuitry of an implantable medical device, cause the processing circuitry to:
electrically connect a first current source to a first electrode of a plurality of electrodes to output an electrical current stimulation pulse to cardiac tissue; and
electrically connect a second current source to a second electrode of the plurality of electrodes to sink the electrical current stimulation pulse,
wherein a cardiac lead comprising the plurality of electrodes is coupled to the implantable medical device,
wherein the implantable medical device is configured to deliver pacing therapy to the cardiac tissue of a heart via the plurality of electrodes of the cardiac lead,
wherein the implantable medical device comprises the first current source configured to output an electrical current stimulation pulse and the second current source configured to sink the electrical current stimulation pulse to capture a portion of the cardiac tissue, and
wherein a first channel of implantable medical device comprises the first current source, the first channel further comprising:
a first switch configured to connect an output terminal of the first current source to the first electrode;
a first recharge switch configured to connect the first electrode to a reference voltage;
a second recharge switch configured to connect the first electrode to the reference voltage through a capacitor; and
a second first channel current source, comprising an input terminal and an output terminal wherein:
the output terminal of the second first channel current source connects to the reference voltage,
the input terminal of the second first channel current source is configured to connect to the first electrode through the capacitor and a second switch, and
the second first channel current source is configured to sink current from the first electrode when the second switch is closed and conducting current.

13. The computer readable storage medium of claim 12, wherein the implantable medical device further comprises a third current source configured to sink the electrical current stimulation pulse, and
wherein instructions further cause the processing circuitry to electrically connect the third current source to a third electrode of the plurality of electrodes to sink the electrical current stimulation pulse to the cardiac tissue, such that the electrical current stimulation pulse captures the portion of the cardiac tissue between the first electrode and the second and the third electrodes.

14. The computer readable storage medium of claim 12, wherein the implantable medical device further comprises a third current source configured to output the electrical current stimulation pulse, and
wherein the processing circuitry is further configured to electrically connect the third current source to a third electrode of the plurality of electrodes to output the electrical current stimulation pulse to the cardiac tissue, such that the electrical current stimulation pulse captures the portion of the cardiac tissue between the third electrode and the second and the first electrodes.

15. The computer readable storage medium of claim 12, wherein the cardiac tissue comprises a left ventricle of the heart.

16. The computer readable storage medium of claim 12, wherein the cardiac tissue comprises one or more of: a right atrium, a right ventricle, Purkinje fibers, bundle of His, and a bundle branch.

17. A medical system comprising:
an implantable medical device coupled to a cardiac lead and configured to deliver pacing therapy to cardiac tissue of a heart via a plurality of electrodes of the cardiac lead, wherein the implantable medical device comprises a first current source configured to output an electrical current stimulation pulse and a second current source configured to sink the electrical current stimulation pulse to capture a portion of the cardiac tissue; and
processing circuitry configured to:
electrically connect the first current source to a first electrode of the plurality of electrodes to output the electrical current stimulation pulse to the cardiac tissue; and
electrically connect the second current source to a second electrode of the plurality of electrodes to sink the electrical current stimulation pulse to the cardiac tissue,
wherein a first channel of implantable medical device comprises the first current source, wherein a second channel of implantable medical device comprises the second current source, wherein the first channel further comprises:
  a first switch configured to connect an output terminal of the first current source to the first electrode; and
  a first recharge switch configured to connect the first electrode to a reference voltage (GND);

wherein the second channel further comprises:
  a second recharge switch configured to connect the second electrode to the reference voltage through a capacitor;
  the second current source comprising an input terminal and an output terminal wherein:
    the output terminal of the second current source connects to the reference voltage,
    the input terminal of the second current source is configured to connect to the second electrode through the capacitor and a second switch, and
    the second current source is configured to sink current from the second electrode when the second switch is closed and conducting current.

* * * * *